US012629159B2

(12) United States Patent
Mobley et al.

(10) Patent No.: US 12,629,159 B2
(45) Date of Patent: May 19, 2026

(54) DISPOSABLE THROMBECTOMY MACERATION AND ASPIRATION SYSTEM

(71) Applicant: Argon Medical Devices, Inc., Frisco, TX (US)

(72) Inventors: Matthew Mobley, Athens, TX (US); Lee Carter, McKinney, TX (US); Mukesh Shah, Des Plaines, IL (US); Ramana Hogirala, Mount Prospect, IL (US)

(73) Assignee: Argon Medical Devices, Inc., Frisco, TX (US)

( * ) Notice: Subject to any disclaimer, the term of this patent is extended or adjusted under 35 U.S.C. 154(b) by 1140 days.

(21) Appl. No.: 17/234,278

(22) Filed: Apr. 19, 2021

(65) Prior Publication Data

US 2022/0330958 A1 Oct. 20, 2022

(51) Int. Cl.
*A61B 17/22* (2006.01)
*A61M 1/00* (2006.01)
*A61B 17/00* (2006.01)

(52) U.S. Cl.
CPC .............. *A61B 17/22* (2013.01); *A61M 1/64* (2021.05); *A61M 1/84* (2021.05);
(Continued)

(58) Field of Classification Search
CPC .......... A61M 1/64; A61M 1/74; A61M 1/741; A61M 1/7411; A61M 1/7413;
(Continued)

(56) References Cited

U.S. PATENT DOCUMENTS 3,138,873 A    6/1964   Bishop
4,883,476 A   11/1989   Kurtz et al.
(Continued)

FOREIGN PATENT DOCUMENTS

DE       29821543 U1    5/1999
WO   2020246431 A1   12/2020

OTHER PUBLICATIONS

European Patent Office, Partial European Search Report, and Provisional Opinion Accompanying tghe Partial Search Report, European Patent Application No. 22165777.8, Sep. 8, 2022, Munich.
(Continued)

*Primary Examiner* — Diane D Yabut
*Assistant Examiner* — Christian D Knauss
(74) *Attorney, Agent, or Firm* — IpHorgan Ltd

(57) ABSTRACT

A disposable thrombectomy maceration and aspiration system for macerating and aspirating thrombus or other obstructive material in a lumen of a vascular graft or vessel. The system includes three major components: a disposable integrated aspiration pump and fluid collection device for generating aspiration vacuum pressure and collecting macerated particulate, a disposable integrated thrombectomy and aspiration apparatus removably coupled to the device configured to macerate the thrombus with a motor powered maceration wire while including an aspiration pathway for aspirating the macerated particulate into the device, and a catheter removably coupled to the apparatus and covering a portion of the maceration wire for insertion into the patient to the thrombus site. The catheter is of sufficient size to allow the macerated particulate to be aspirated from a distal opening through the catheter and apparatus before being deposited into the fluid collection compartment of the device.

41 Claims, 28 Drawing Sheets

(52) U.S. Cl.
CPC .............. *A61B 2017/00199* (2013.01); *A61B 2017/0023* (2013.01); *A61B 2017/22079* (2013.01); *A61B 2217/005* (2013.01)

(58) Field of Classification Search
CPC .... A61M 1/7415; A61M 1/742; A61M 1/743; A61B 17/22; A61B 17/3207; A61B 17/320775; A61B 2017/00199; A61B 2017/22079; A61B 2017/320064; A61B 2217/005; A61B 17/320758
See application file for complete search history.

(56) References Cited

U.S. PATENT DOCUMENTS

| | | | |
|---|---|---|---|
| 5,192,439 | A | 3/1993 | Roth et al. |
| 5,827,229 | A | 10/1998 | Auth et al. |
| 7,037,316 | B2 | 5/2006 | McGuckin, Jr. |
| 7,507,246 | B2 | 3/2009 | McGuckin et al. |
| 7,645,290 | B2 | 1/2010 | Lucas |
| 8,070,735 | B2 | 12/2011 | Koch et al. |
| 9,095,326 | B2 | 8/2015 | Ritchie et al. |
| 9,474,543 | B2 | 10/2016 | McGuckin, Jr. et al. |
| 10,226,263 | B2 | 3/2019 | Look |
| 10,531,883 | B1 | 1/2020 | Deville et al. |
| 2004/0019358 | A1* | 1/2004 | Kear ............... A61B 17/22031 606/127 |
| 2004/0024360 | A1 | 2/2004 | Greter |
| 2005/0222527 | A1* | 10/2005 | Miller .................... A61F 13/05 602/1 |
| 2006/0253145 | A1* | 11/2006 | Lucas ................... A61B 17/22 606/159 |
| 2010/0094201 | A1 | 4/2010 | Mallaby |
| 2012/0116429 | A1 | 5/2012 | Levine |
| 2015/0165100 | A1* | 6/2015 | Feltyberger ............. A61M 1/69 604/67 |
| 2017/0028110 | A1 | 2/2017 | Smith |
| 2017/0049470 | A1 | 2/2017 | Mallaby |
| 2017/0273698 | A1* | 9/2017 | Mcguckin, Jr. ........ A61B 17/22 |
| 2017/0319758 | A1* | 11/2017 | Eddy ....................... A61M 1/81 |
| 2018/0353194 | A1* | 12/2018 | Shaffer .................. A61B 17/22 |
| 2018/0368965 | A1* | 12/2018 | Janardhan ............... A61M 1/84 |
| 2019/0336149 | A1* | 11/2019 | Yang ................. A61M 25/0012 |
| 2020/0367917 | A1 | 11/2020 | Teigen et al. |
| 2022/0241485 | A1 | 8/2022 | Nakagawa |

OTHER PUBLICATIONS

European Patent Office, European Search Report, European Patent Application No. 22165777.8, Mar. 29, 2023, The Hague.
European Patent Office, European Search Opinion, European Patent Application No. 22165777.8, Mar. 29, 2023, The Hague.

* cited by examiner

DISPOSABLE THROMBECTOMY MACERATION AND ASPIRATION SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to disposable thrombectomy maceration systems and thrombectomy aspiration systems. More specifically disposable thrombectomy maceration systems utilizing maceration wires and aspiration.

(2) Description of Related Art Including Information Disclosed Under 37 CFR 1.97 and 1.98

The prior art relates to mechanical thrombectomy apparatuses, some apparatuses use maceration and some use aspiration. U.S. Pat. Nos. 7,507,246 and 9,474,543 are both directed to a rotational thrombectomy wire for breaking up thrombus or other obstructive material, both of which are incorporated herein by reference.

BRIEF SUMMARY OF THE INVENTION

An embodiment of the disclosure meets the needs presented above by generally comprising a disposable thrombectomy maceration and aspiration system for macerating and aspirating thrombus or other obstructive material in a lumen of a vascular graft or vessel. The system includes three major components.

The first is a disposable integrated aspiration pump and fluid collection device which includes a base, a pump, a fluid collection compartment and a controller capable of pulling a vacuum to aspirate macerated particulate.

The second is a disposable integrated thrombectomy and aspiration apparatus removably coupled to the disposable integrated aspiration pump and fluid collection device. The apparatus has a maceration wire, a motor operatively connected to the maceration wire, and an aspiration pathway coupled to the first device. At least a portion of the aspiration pathway includes an annular portion including a portion of the maceration wire whereby the macerated particulate may be aspirated from the patient. At least a portion of the annular pathway is slidable in relation to the maceration wire. The maceration wire extends through the apparatus to enter the third component, a catheter.

The catheter is removably coupled to the apparatus and covers a portion of the maceration wire. The catheter further includes a flexible sheath extending away from the apparatus. The catheter is of sufficient size to allow the macerated particulate to be aspirated from a distal opening through the catheter and apparatus before being deposited into the fluid collection compartment of the device.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
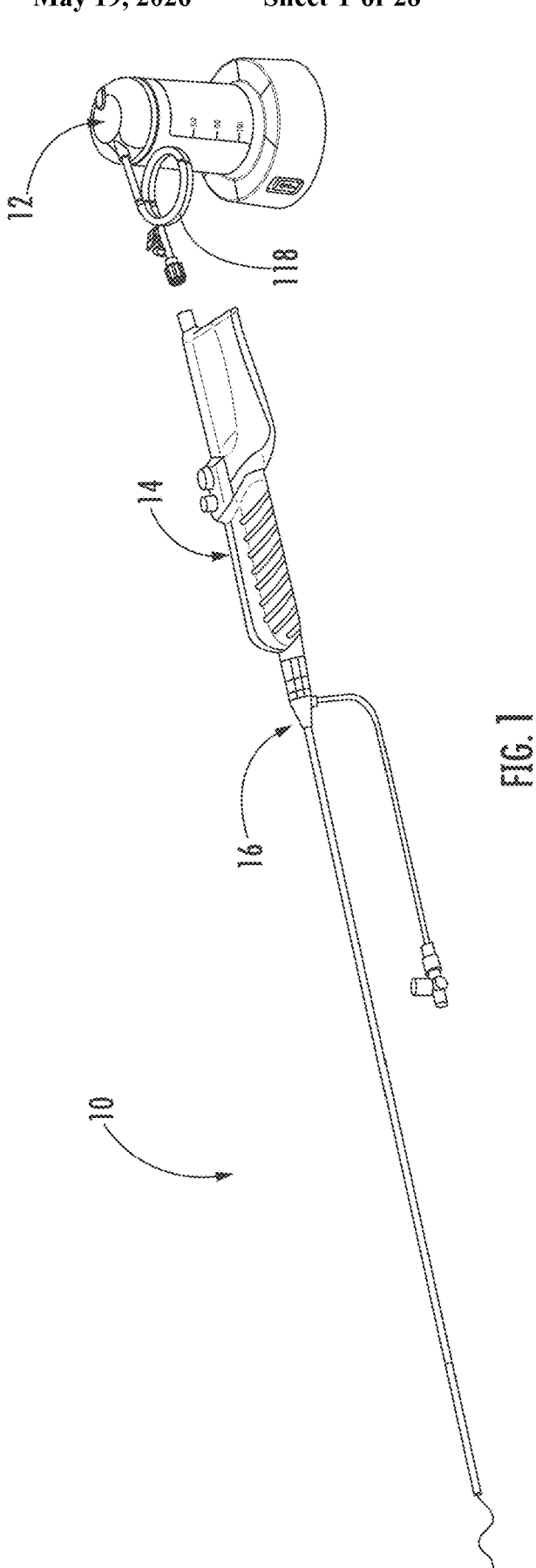
FIG. 1 is an isometric view of a disposable thrombectomy maceration and aspiration system according to an embodiment of the disclosure, illustrating the major components.

With reference now to the drawings, and in particular to FIGS. 1 through 33 thereof, a new thrombectomy system embodying the principles and concepts of an embodiment of the disclosure and generally designated by the reference numeral 10 will be described.

As best illustrated in FIGS. 1 through 6, the invention generally comprises a disposable thrombectomy maceration and aspiration system 10 for macerating and aspirating thrombus or other obstructive material in a lumen of a vascular graft or vessel. The system 10 comprising three components: a disposable integrated aspiration pump and fluid collection device 12, a disposable integrated thrombectomy and aspiration apparatus 14, and a catheter 16. As shown in FIG. 1 the catheter 16 and apparatus 14 couple together directly while the apparatus 14 and device 12 may be connected via a connection catheter 118.

Disposable Integrated Aspiration Pump and Fluid Collection Device:

The disposable integrated aspiration pump and fluid collection device 12 has a base 18, and the base 18 has a base compartment 20. The base 18 may be made from any rigid material structurally capable of supporting the device 12. Suitable rigid materials may include plastics, metals, composites, or other natural and artificial materials which are commercially available.

Figure 15:
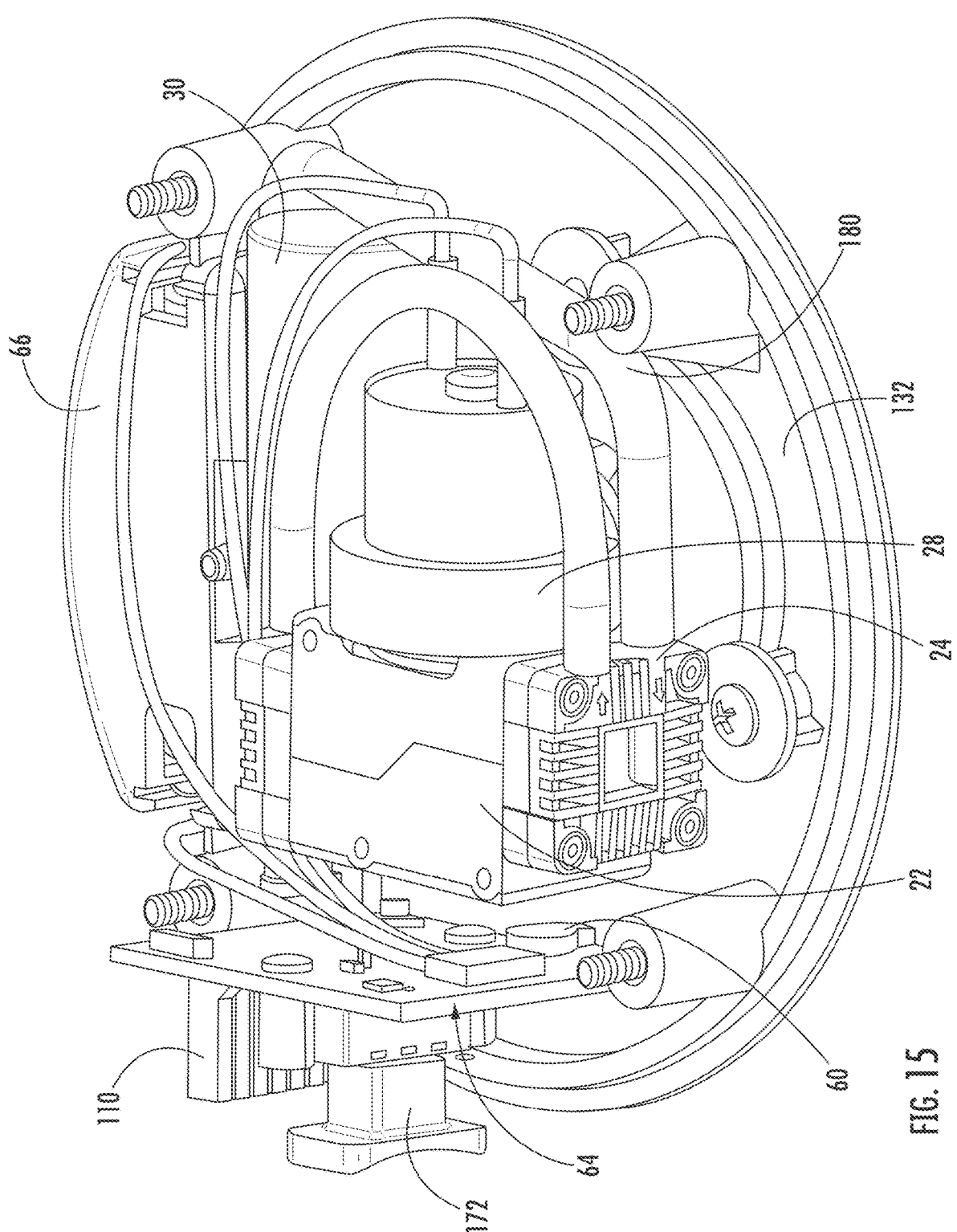
FIG. 15 is a top left isometric view of an embodiment of the components within the base compartment with the base compartment not shown to illustrate the internal layout of the pump and components as described in the disclosure.

A pump 22, located in the base compartment 20, has an intake port 24 and an exhaust port 26. The pump 22 is designed to operate at a relatively low flow rate but to exert a large vacuum pressure. The pump flow rate in the present embodiment is configured to operate over 1.5 liters per minute (L/min) and to exert a vacuum pressure between 5 inHg and absolute vacuum, where absolute vacuum is 0 inHg. As shown in FIG. 15, the pump 22 in the present embodiment is attached to the base 18 by a pump mount 28. The pump 22 may include additional features, such as a silencer 30, to reduce the noise or provide additional benefits for the user. The pump 22 is designed to be disposable and compact to reduce the size needed for the base compartment 20 and to reduce the costs associated with long-use pumps of a similar nature that are commercially available. In the present embodiment, the pump utilizes diaphragm pumping technology to reduce the costs, while maintaining the high vacuum pressures.

Figure 3:
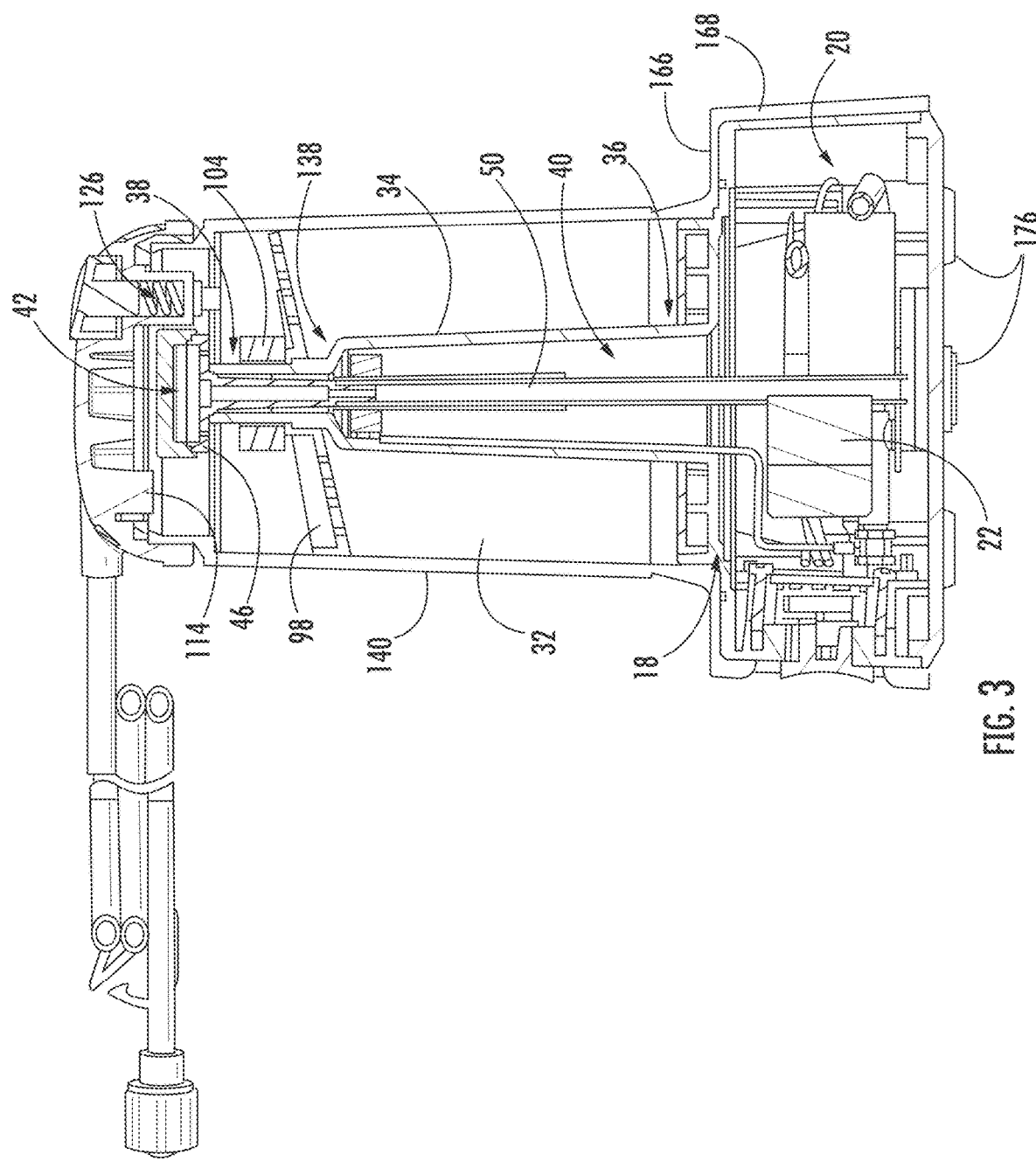
FIG. 3 is a cross sectional view of an embodiment of the disposable integrated aspiration pump and fluid collection device described in the disclosure, illustrating the internal features of the device.

As shown in FIG. 3, a fluid collection compartment 32 is located above the base 18. A column 34 extends within the fluid collection compartment 32 in substantially a vertical direction. The column 34 has a lower portion 36 and an upper portion 38 and forms a cavity 40 within the column 34. The cavity 40 in the column 34 is in fluid communication with the base compartment 20 and is closed off at the upper portion 38. The fluid collection compartment 32 will collect the macerated particulate, or other removed material, pulled into the fluid collection compartment 32 by the vacuum pressure the pump 22 creates.

Figure 14:
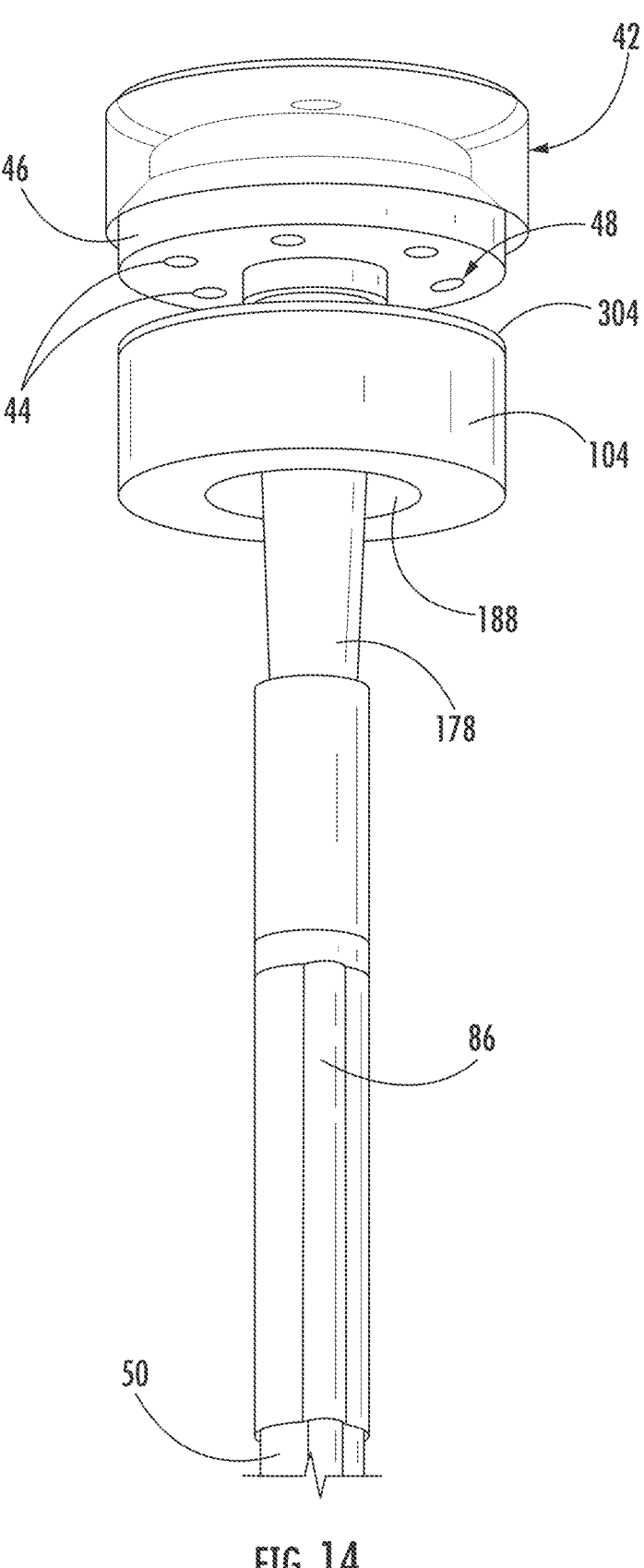
FIG. 14 is a bottom left isometric view of an embodiment of the float shut-off mechanism to illustrate the features without showing the column.

A manifold 42 is located at the upper portion 38 of the column 34 and includes one or more inlets 44. The manifold 42 has a generally disc shaped portion 46 and the disc shape portion 46 has a lower surface 48 which includes the inlets 44, whereby the inlets 44 face in a downward direction as shown in FIG. 14. The inlets 44 are configured to allow the vacuum pressure to be applied to the fluid collection compartment 32 while minimizing the chance of fluids entering the pump 22.

A suction tube 50, which has a first end 52 and a second end 54, is found within the column 34. The first end 52 of the suction tube 50 is in fluid communication with the intake port 24 of the pump 22. The suction tube 50 then extends substantially vertically through the cavity 40 of the column 34 where the second end 54 of the suction tube 50 is in fluid communication with the inlets 44 on the manifold 42. The suction tube 50 may be made of any suitable material which is rigid enough to not collapse under the vacuum pressure. Suitable materials may include plastics, metals, composites, or other natural and artificial materials commercially available. The suction tube 50 may be operably attached to the intake port 24 of the pump 22 by any mechanical means sufficient to prevent detachment while maintaining a seal needed to maintain the vacuum pressure in the fluid collection compartment 32.

Figure 19:
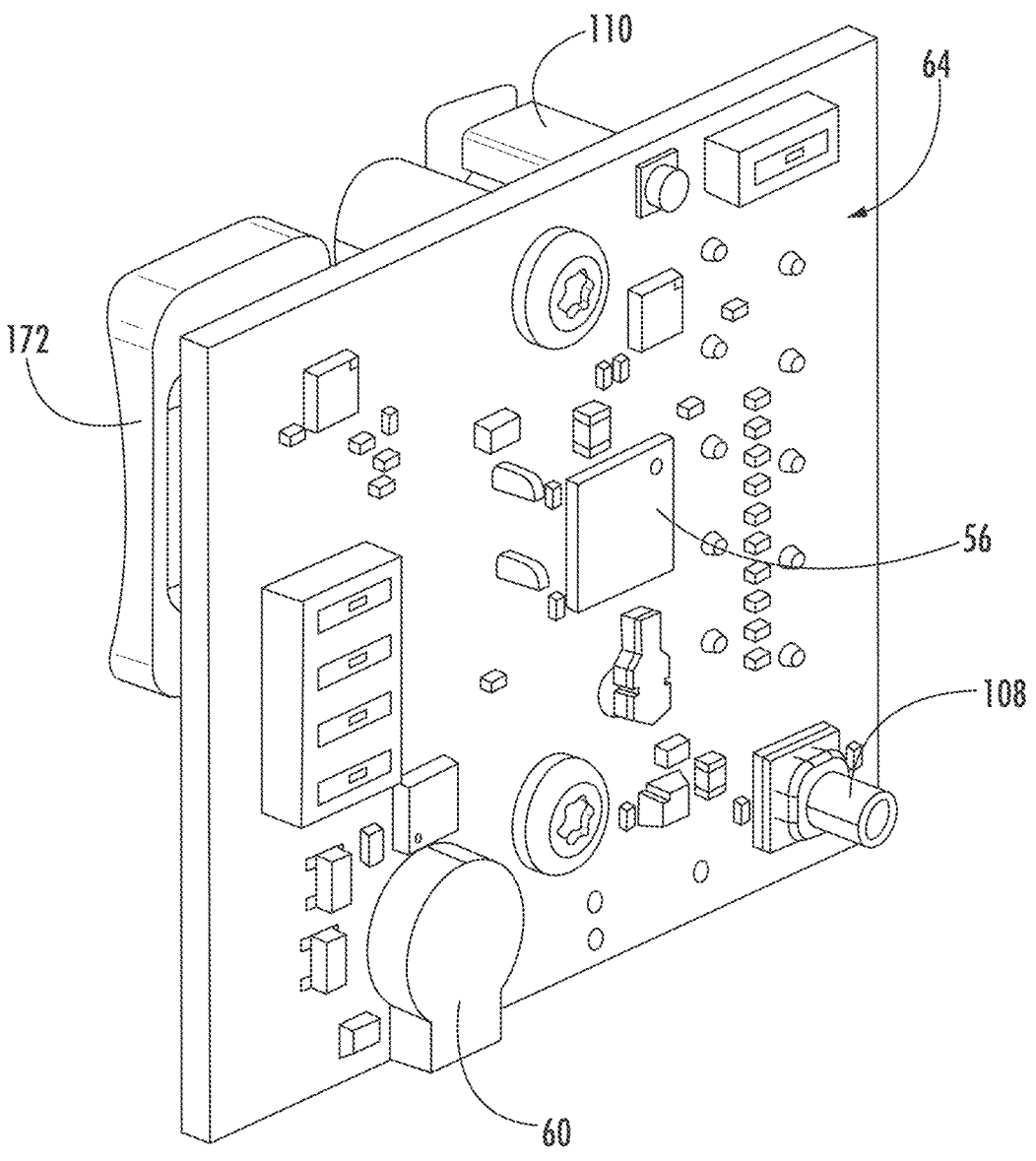
FIG. 19 is a rear left isometric view of an embodiment of the PCB board as described in the disclosure.
Figure 22:
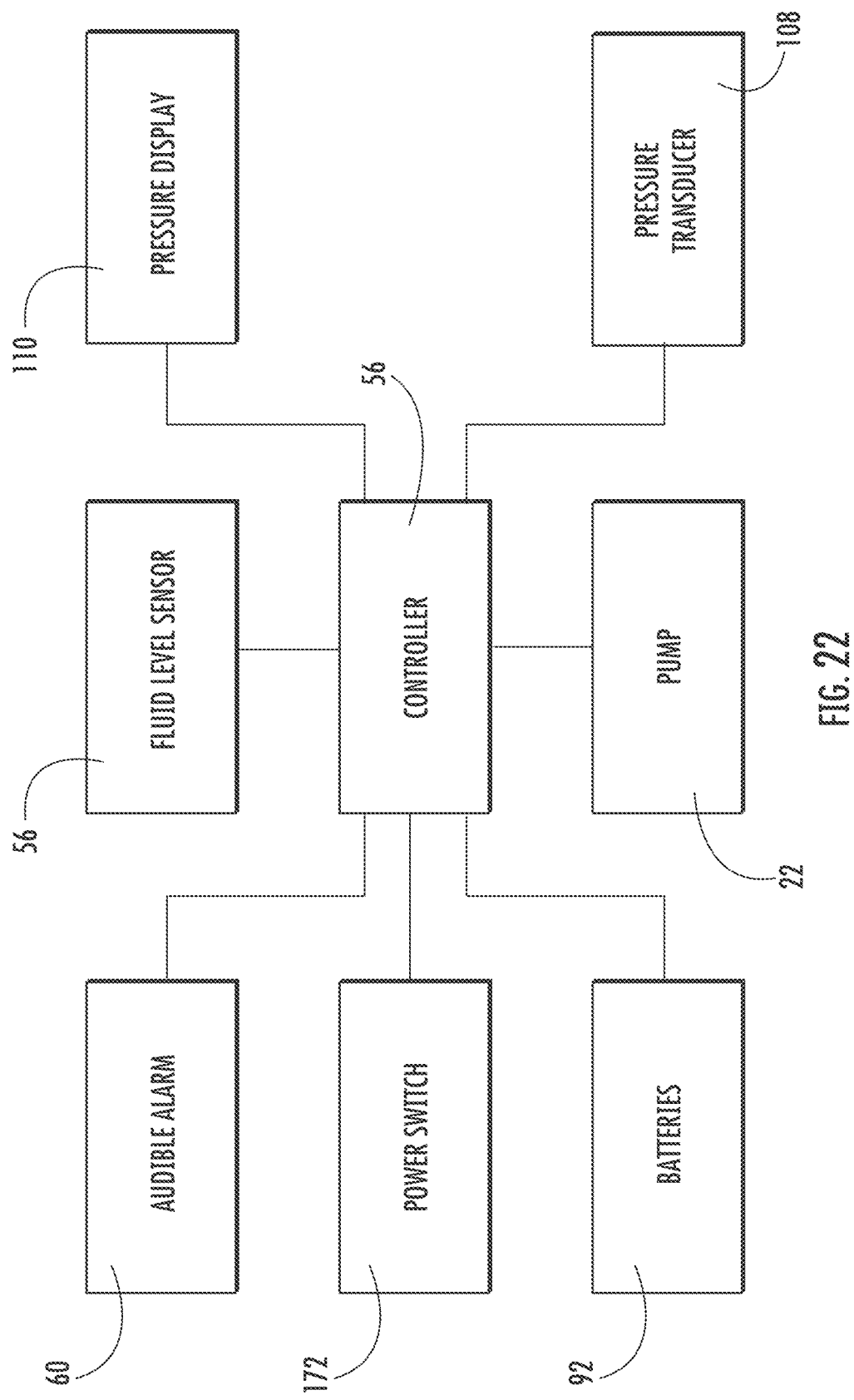
FIG. 22 is an electronic diagram of the components connected to the controller in an embodiment of the disclosure.

A controller 56 is also located in the base compartment 20 of the base 18. The controller 56 is electronically coupled to a fluid level sensor 58 and an audible alarm 60. The fluid level sensor 58 is located at a designated sensor elevation 62 within the fluid collection compartment 32. The fluid level sensor 58 detects the presence of fluid at the designated sensor elevation 62 and communicates that status to the controller 56. The controller 56 includes a means to activate the audible alarm 60 for a preset amount of time when the fluid level sensor 58 detects fluid at the designated sensor elevation 62, and at the end of the preset amount of time, the controller mechanism shuts off the pump 22. This shut-off on the controller 56 allows for the device 12 to automatically shut off the pump 22 while notifying the user of both the status of the fluid collection compartment 32 and the impending loss of vacuum. This feature allows the user to focus on the procedure and to continue to operate once the audible alarm 60 is heard to get to the safest position possible for the patient before the pump 22 is shut off and the vacuum is lost. While the fluid collection compartment 32 may be visible during use, the fluid level sensor 58 reduces the need to visually check on the fluid level to prevent overfilling. If a procedure would require continued use, the full device 12 can be removed and a second disposable integrated aspiration pump and fluid collection device 12 could be coupled to continue with the procedure without having to remove the catheter 16 from the patient. FIG. 19 illustrates how the controller 56 may be a part of a larger Printed Circuit Board (PCB) 64 wherein the audible alarm 60 and other components are coupled to the controller 56 via the PCB 64. FIG. 22 is an illustrative diagram of the components electronically coupled to the controller 56.

The fluid level sensor 58 in the present embodiment includes a non-contact capacitance sensor. The fluid level sensor 58 is located on an inner surface 68 of the column 34.

Figure 12:
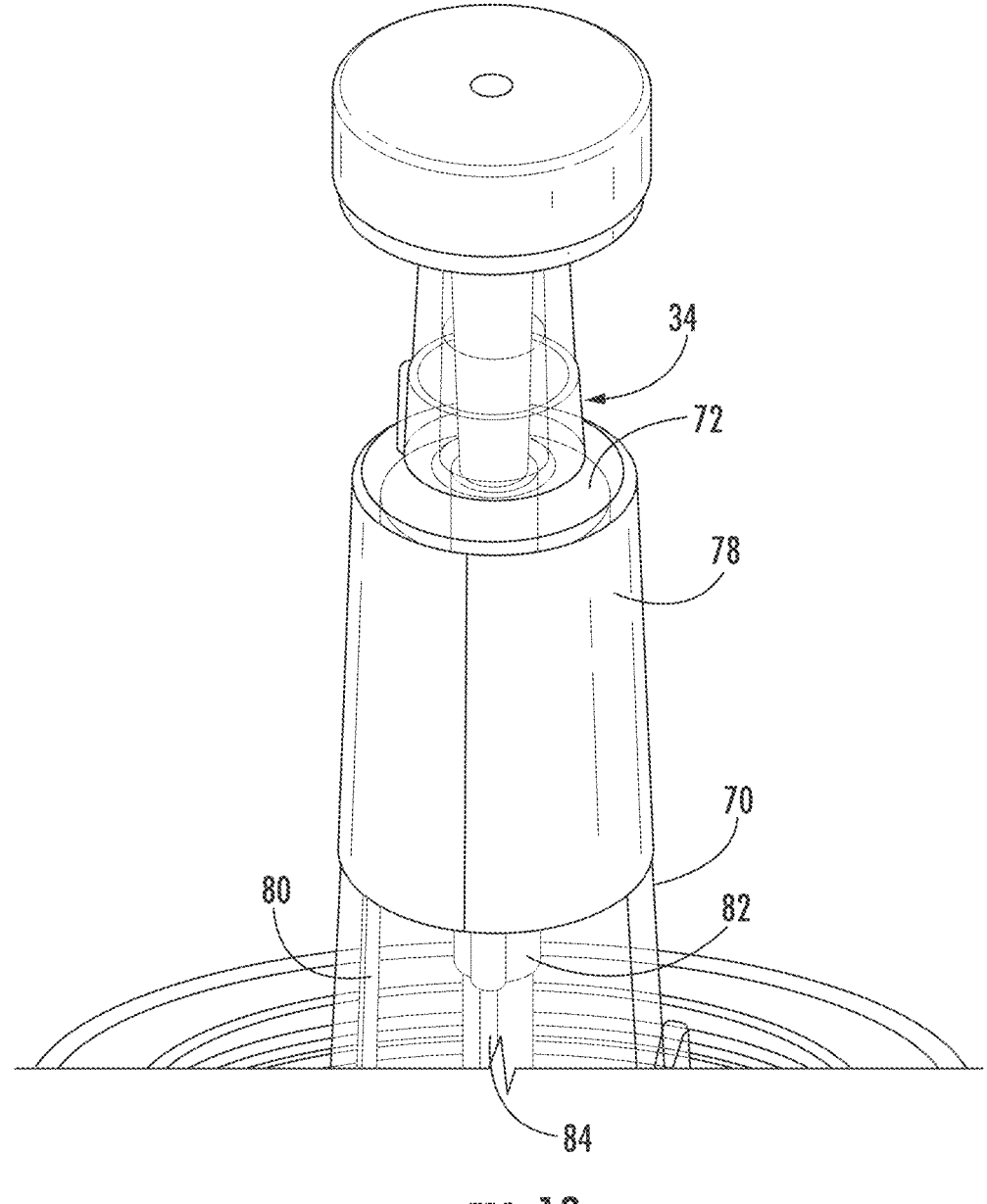
FIG. 12 is a top left isometric view of various features of an embodiment of the column as described in the disclosure.
Figure 13:
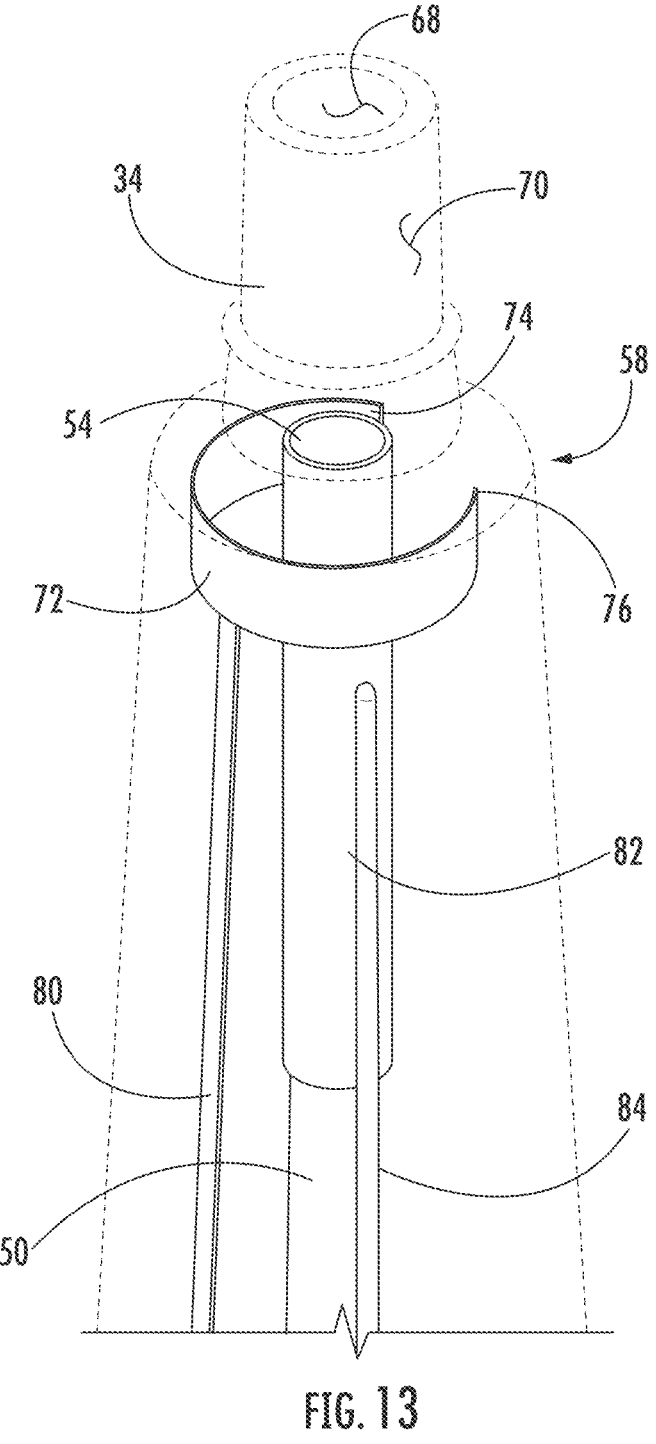
FIG. 13 is a top left isometric view of an embodiment of the fluid level sensor within the column to illustrate the features as described in the disclosure.

The column 34 also has an outer surface 70. The fluid level sensor 58 includes a strip of copper 72 with a first 74 end and a second 76 end and is located on the inner surface 68 of the column 34 extending around a portion of the circumference of the inner surface 68 of the column 34, as illustrated in FIG. 13. The strip of copper 72 forms a gap between the first 74 and second 76 ends of the strip of cooper 72. FIG. 12 illustrates where a hydrophobic film 78 is located on at least a portion of the outer surface 70 of the column 34. The hydrophobic film 78 repels the macerated fluids to reduce the chance of the fluid level sensor 58 picking up temporary increases in the fluid level. Scenarios where this may occur is if the device 12 is bumped or the aspirated particulate splashes to the designated sensor elevation 62.

A sensor wire 80 couples the strip of copper 72 to the controller 56. A portion of the suction tube 50 extends within the cavity 40 of the column 34 and is covered by a shielding material 82. A shielding wire 84 with a first end 86 and a second end 88 with the first end 86 of the shielding wire 84 being coupled to ground on the controller 56 and the second end 88 of the shielding wire 84 being coupled to the shielding material 82. The shielding wire 84 helps focus the fluid level sensor 58 on sensing outside the column 34. The fluid level sensor 58 as shown in the present embodiment is only one method for sensing fluid levels through an adjacent wall. Other commercially available methods, such as an inductive field, could also be implemented to provide the same benefit.

The base compartment 20 also has a battery compartment 66 and battery contacts 90 for receiving one or more batteries 92. The battery contacts 90 couple the batteries 92 to the controller 56 to provide power. The base 18 also has a battery door 94 for removing and disposing of the batteries 92 separate from the device 12 and a vent 96 in fluid communication with the base compartment 20 and ambient air. The batteries 92 may be rechargeable or disposable. Suitable batteries 92 may include dry cell, lithium-ion, nickel metal hydride or other commercially available batteries capable of powering the device 12. In the present embodiment, lithium CR2 batteries 92 are shown.

Figure 8:
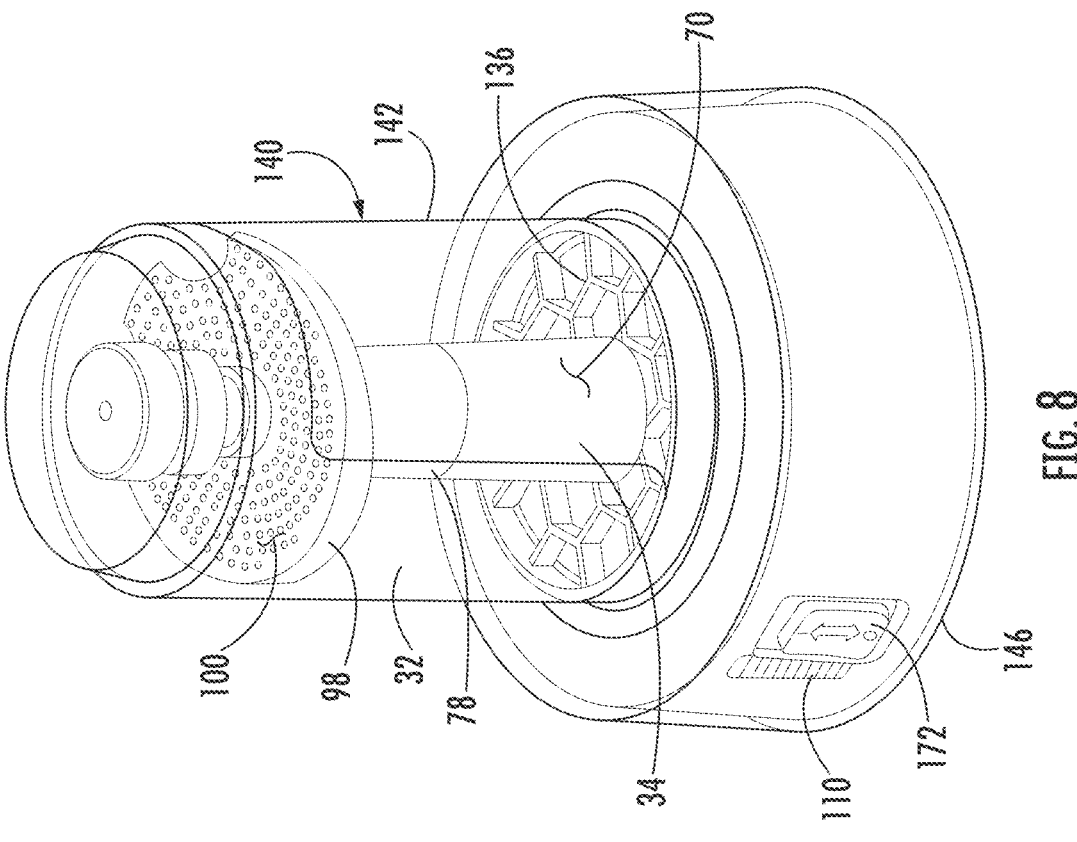
FIG. 8 is a top left isometric view of an embodiment of the disposable integrated aspiration pump and fluid collection device without the lid as described in the disclosure illustrating the canister housing being a transparent material.
Figure 7:
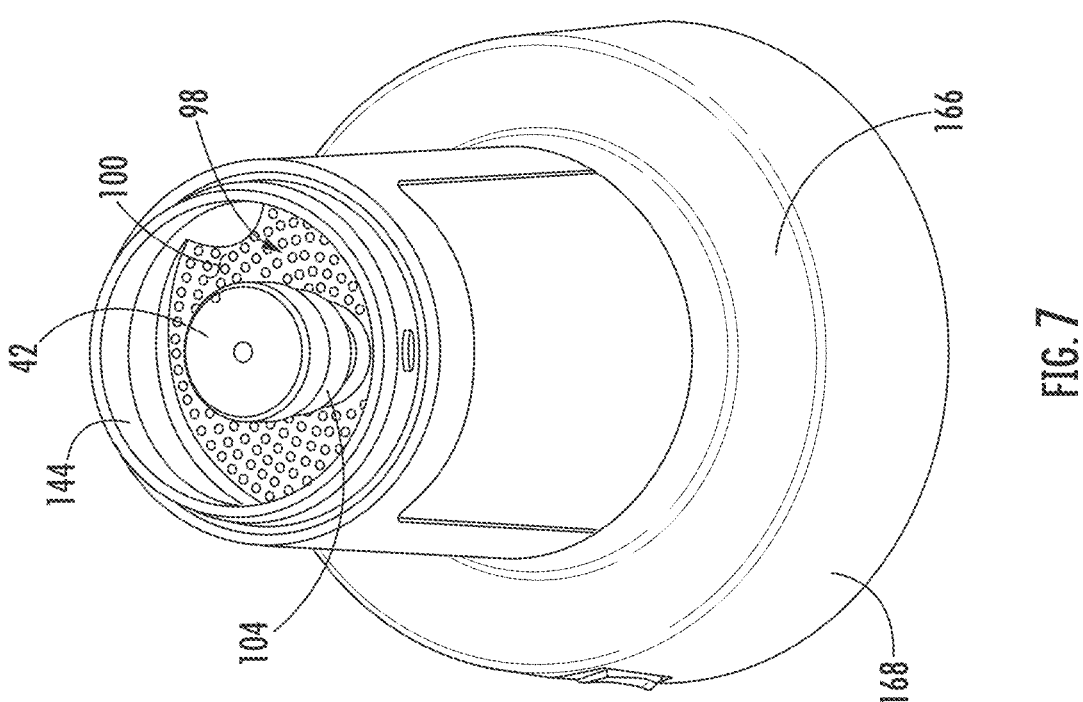
FIG. 7 is a top left isometric view of an embodiment of the disposable integrated aspiration pump and fluid collection device without the lid as described in the disclosure.

Illustrated in FIG. 8, a fluid filter 98 located within the fluid collection compartment 32 may also be included in the device 12. The fluid filter 98 has a fluid permeable ledge 100 to allow a portion of the macerated thrombus to remain on the fluid filter 98 for observation while the liquid portions of the aspirated materials will pass through to the fluid collection compartment 32. This observation aids the user in evaluating the type of materials being aspirated and allows for additional visibility when the aspirated fluids may otherwise obscure the macerated materials. FIG. 8 illustrates how the fluid filter 98 also reduces access of tools or equipment into the fluid collection compartment 32 to prevent attempts at re-sterilization and reuse. The fluid filter 98 may be made of a structurally rigid material capable of withstanding the necessary forces. Examples of suitable rigid materials may include plastics, metals, composites, or other natural and artificial materials which are commercially available.

Figure 9:
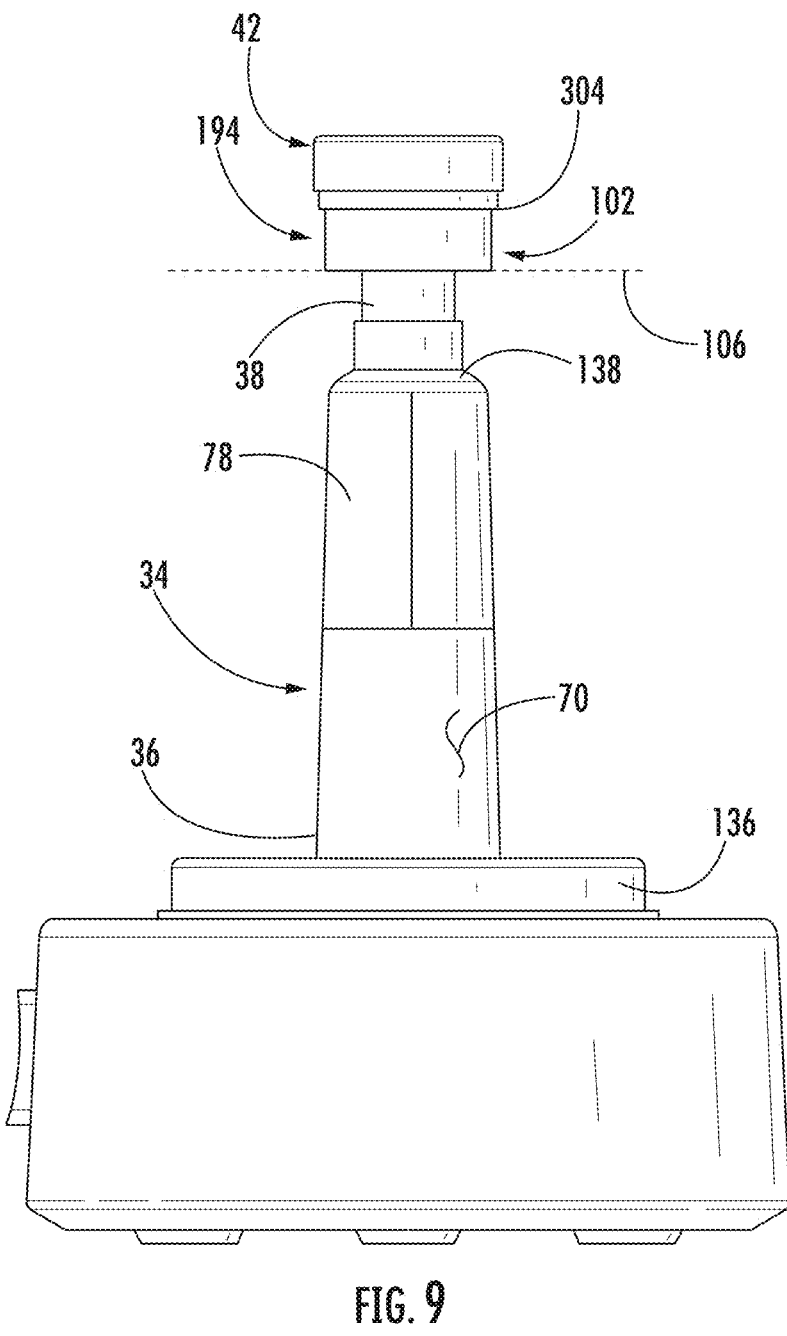
FIG. 9 is a left side view of an embodiment of the disposable integrated aspiration pump and fluid collection device without the canister housing and lid as described in the disclosure.
Figure 10:
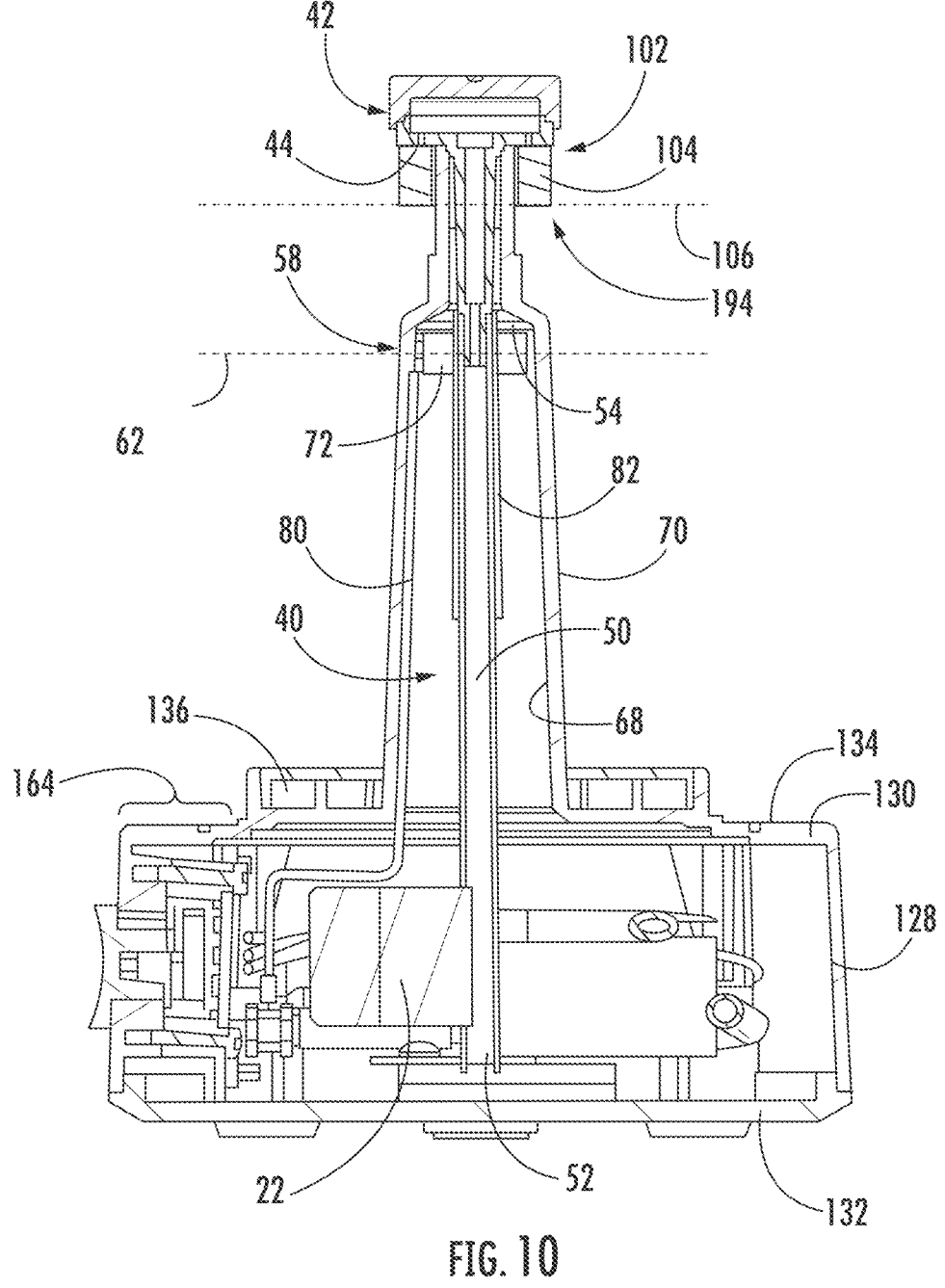
FIG. 10 is a left side section view of an embodiment of the disposable integrated aspiration pump and fluid collection device without the canister housing and lid as described in the disclosure to illustrate the internal features.
Figure 11:
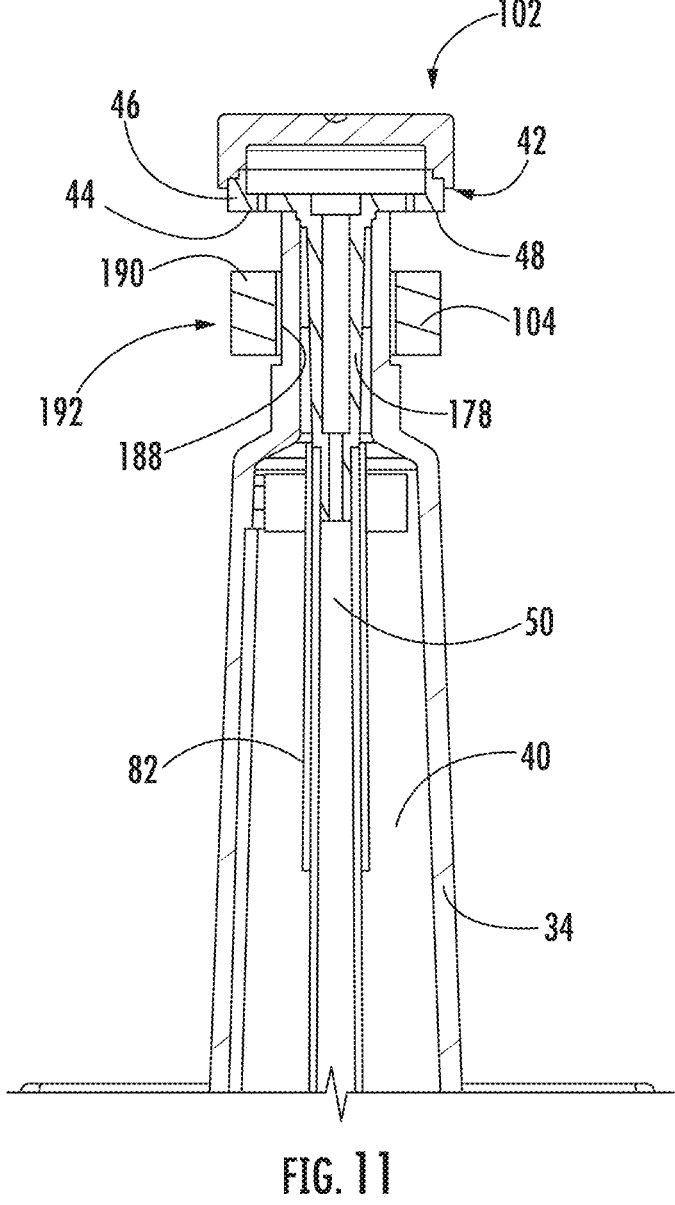
FIG. 11 is a left side section view of an embodiment of the column located within the fluid collection compartment as described in the disclosure.

A float shut-off mechanism 102 is configured to mechanically seal the suction tube 50 off from the fluid collection compartment 32 should the fluid collection compartment 32 fill up and the fluid level sensor 58 fail to shut off the pump 22. The float shut-off mechanism 102 includes a float 104 located below the inlets 44 of the manifold 42, whereby when the level of fluid rises and raises the float 104 to a designated maximum fluid elevation 106, the float 104 will engage the inlets 44 and close off the fluid communication between the inlets 44 and the fluid collection compartment 32. An embodiment of the invention may further include a seal layer 304 fixed to the float 104 to provide improved engagement to close off the fluid communication between the inlets 44 and the fluid collection compartment 32. FIG. 9 illustrates the location of the seal layer 304 adjacent to the manifold 42 when the float 104 is in a shut-off level position 194 at the designated maximum fluid elevation 106. The need for a mechanical backup to the electronic fluid level sensor 58 shut-off is another safety measure to protect the patient from over-aspiration. From a product design standpoint the float shut-off mechanism 102 also prevents the pump 22 from pulling aspirated materials into the pump 22 itself through the suction tube 50.

A pressure transducer 108 and a pressure display 110 are located in the base compartment 20 and coupled to the controller 56. The pressure transducer 108 is in fluid communication with the suction tube 50. The controller 56 includes a means of determining the pressure measured at the pressure transducer 108 and displaying the measured pressure on the pressure display 110. To maximize the pressure, the controller 56 includes means for operating the pump 22 to regulate the pressure wherein the controller 56 regulates the pressure to a preset maximum vacuum and accordingly displays the preset maximum vacuum pressure on the pressure display 110. The pressure display 110 may consist of a segment bar display.

The function of the pressure transducer 108 and pressure display 110 allows the user a means of verifying the pressure being applied by the pump 22. The pressure display 110 may use any commercially available means of conveying these conditions. Examples include LEDs, LCDs, digital readouts, and other visible means of communication. In the present embodiment, the pressure display 110 uses the segment bar display method wherein an initial bar indicates the device 12 has been activated and sequential bars are illuminated to indicate the relative pressure sensed by the pressure transducer 108 with the final bar in the sequence indicating maximum pressure being sensed.

Figure 6:
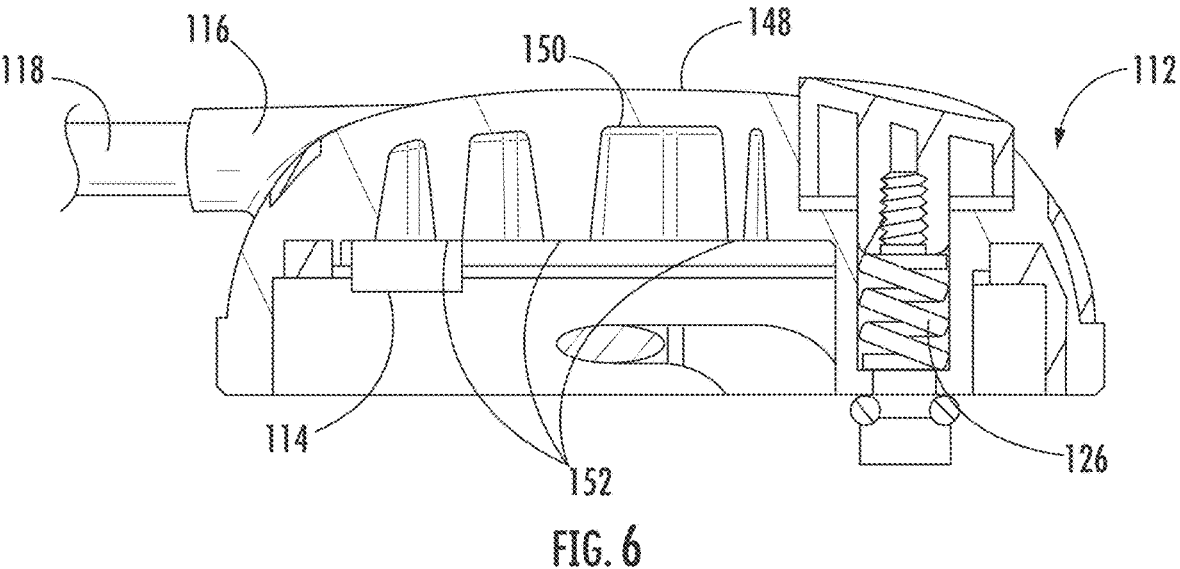
FIG. 6 is a cross sectional view of an embodiment of the lid as described in the disclosure.

A lid 112 closing off the top of the fluid collection compartment 32 may be included in the device 12. The lid 112 is removable to expose the interior of the fluid collection compartment 32. A suction port 114 in fluid communication with the fluid collection compartment 32 is attached to the lid 112. FIG. 6 illustrates how the suction port 114 has a catheter fitting 116 for coupling to catheters, whereby the catheter may be connected to another medical device. In the present embodiment, the catheter is the connection catheter 118, which is used to couple the device 12 to the apparatus 14. However, the catheter may also be a traditional catheter used to aspirate within the patient. Additionally, the catheter may simply be a connecting tube used to couple the device 12 to a medical device that requires aspiration.

Figure 2:
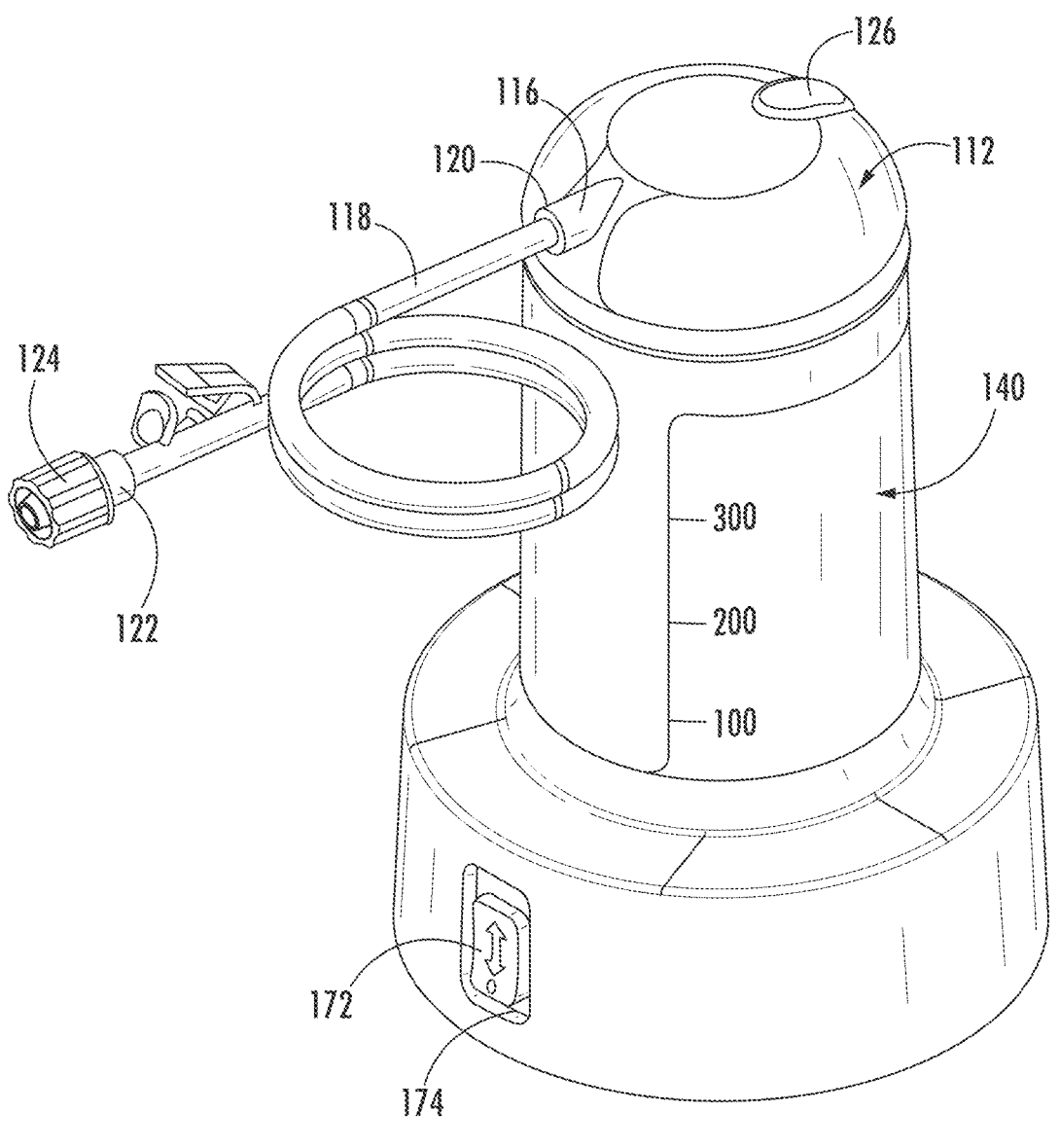
FIG. 2 is an isometric view of an embodiment of the disposable integrated aspiration pump and fluid collection device described in the disclosure.

The catheter fitting 116 extends from the lid 112 in a horizontal direction to provide a low profile, and optionally includes the connection catheter 118 with a first end 120 and a second end 122. The first end 120 of the connection catheter 118 is secured to the catheter fitting 116 and the second end 122 of the connection catheter 118 has an aspiration coupling 124. FIG. 2 illustrates how the lid 112 and connection catheter 118 project horizontally and an additional option wherein the connection catheter 118 may coil up to save space during packaging and transportation. The connection catheter 118 may be any suitable connection tube of medical grade, examples including catheters and other commercially available tubes used in medical devices. The aspiration coupling 124 in the present embodiment is used to removably couple the device 12 to the disposable integrated thrombectomy and aspiration apparatus 14. A manually operated pressure equilibration valve 126 may be secured to the fluid collection compartment 32 wherein when operated it will equalize the pressure in the fluid collection compartment 32 to ambient pressure. The pressure equilibration valve 126 allows for easier removal of the lid 112 from the device 12 by removing the vacuum from within the fluid collection compartment 32.

Figure 20:
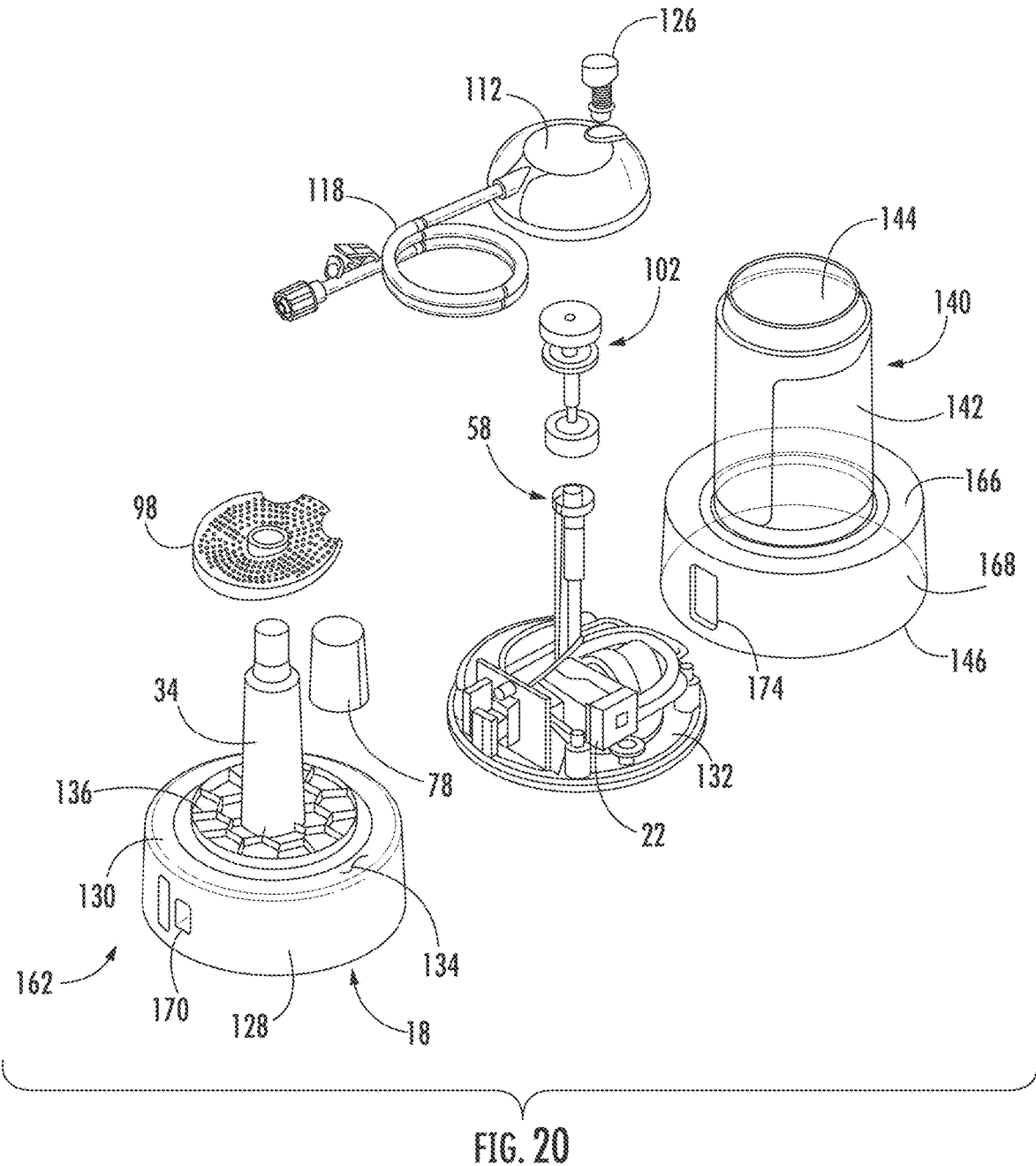
FIG. 20 is a top left isometric exploded view of an embodiment of the disposable integrated aspiration pump and fluid collection device as described in the disclosure to illustrate the components as assembled.

In the present embodiment, the base 18 includes a base sidewall 128 and a base top wall 130, and base bottom wall 132 which define the base compartment 20. The column 34 extends vertically from the base top wall 130. The base top wall 130 includes an upper surface 134 surrounding the column 34 and includes a first ribbed pattern 136 which rises above the upper surface 134 of the base top wall 130. The first ribbed pattern 136 is configured to dissuade attempts at reusing the device 12 by confirming re-sterilization is problematic. The first ribbed pattern 136 may be any pattern or feature capable of accomplishing this goal, including a hexagon pattern, a honeycomb pattern, a wavy pattern, a crosshatch pattern, or other conceivable pattern wherein re-sterilization is made more difficult when compared to a smooth flat surface. As shown in FIG. 20, the first ribbed pattern 136 is a hexagon pattern in the present embodiment.

In the present embodiment shown in FIG. 3, the column 34 is generally cylindrical and includes the lower portion 36 and the upper portion 38. The lower portion 36 of the column 34 has a tapered profile in the vertical direction. The lower portion 36 of the column 34 and the upper portion 38 of the column 34 are separated by a stepped portion 138. In the present embodiment the fluid filter 98 is located on the column 34 at the stepped portion 138. The upper portion 38 includes a tapered profile in the vertical direction with the manifold 42 secured to the upper portion 38 of the column 34.

Figure 5:
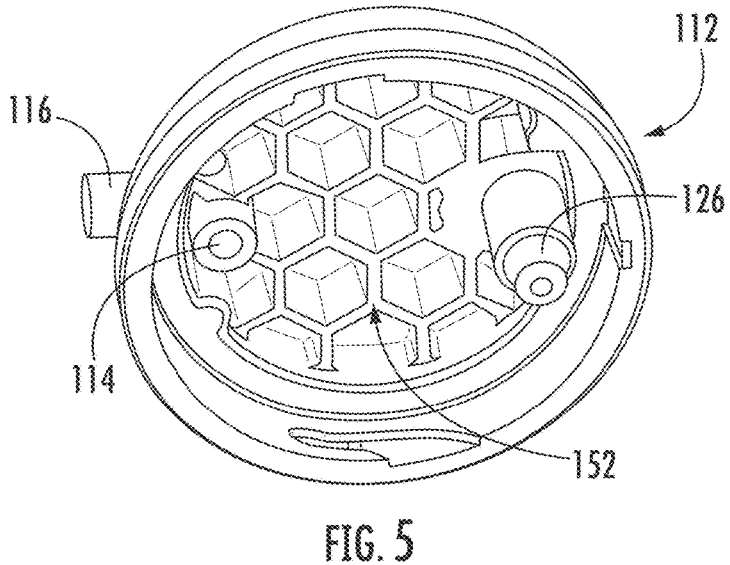
FIG. 5 is a bottom isometric view of an embodiment of the lid described in the disclosure illustrating the second ribbed pattern.

The device 12 may further include a canister housing 140 made of a transparent material to aid in visibility of the macerated particulate. The canister housing 140 has a main cylindrical portion 142 with an open top end 144 and an open bottom end 146 as best illustrated in FIG. 20. The open bottom end 146 of the canister housing 140 is closed by the base 18. The removable lid 112 seals the open top end 144. The lid 112 includes an upper surface 148 and a lower surface 150. The lower surface 150 of the lid 112 includes a second ribbed pattern 152 which extends below the lower surface 150 of the lid 112. The main cylindrical portion 142 of the canister housing 140, the lid 112, the upper surface 134 of the base top wall 130, and the column 34 of the base 18 define the fluid collection compartment 32. The second ribbed pattern 152 is configured to dissuade attempts at reusing the device 12 by confirming re-sterilization is problematic. The second ribbed pattern 152 may be any pattern or feature including a hexagon pattern, a honeycomb pattern, a wavy pattern, a crosshatch pattern, or other conceivable pattern wherein re-sterilization is made more difficult when compared to a smooth flat surface. FIG. 5 illustrates that the second ribbed pattern 152 is a hexagon pattern in the present embodiment.

Figure 21:
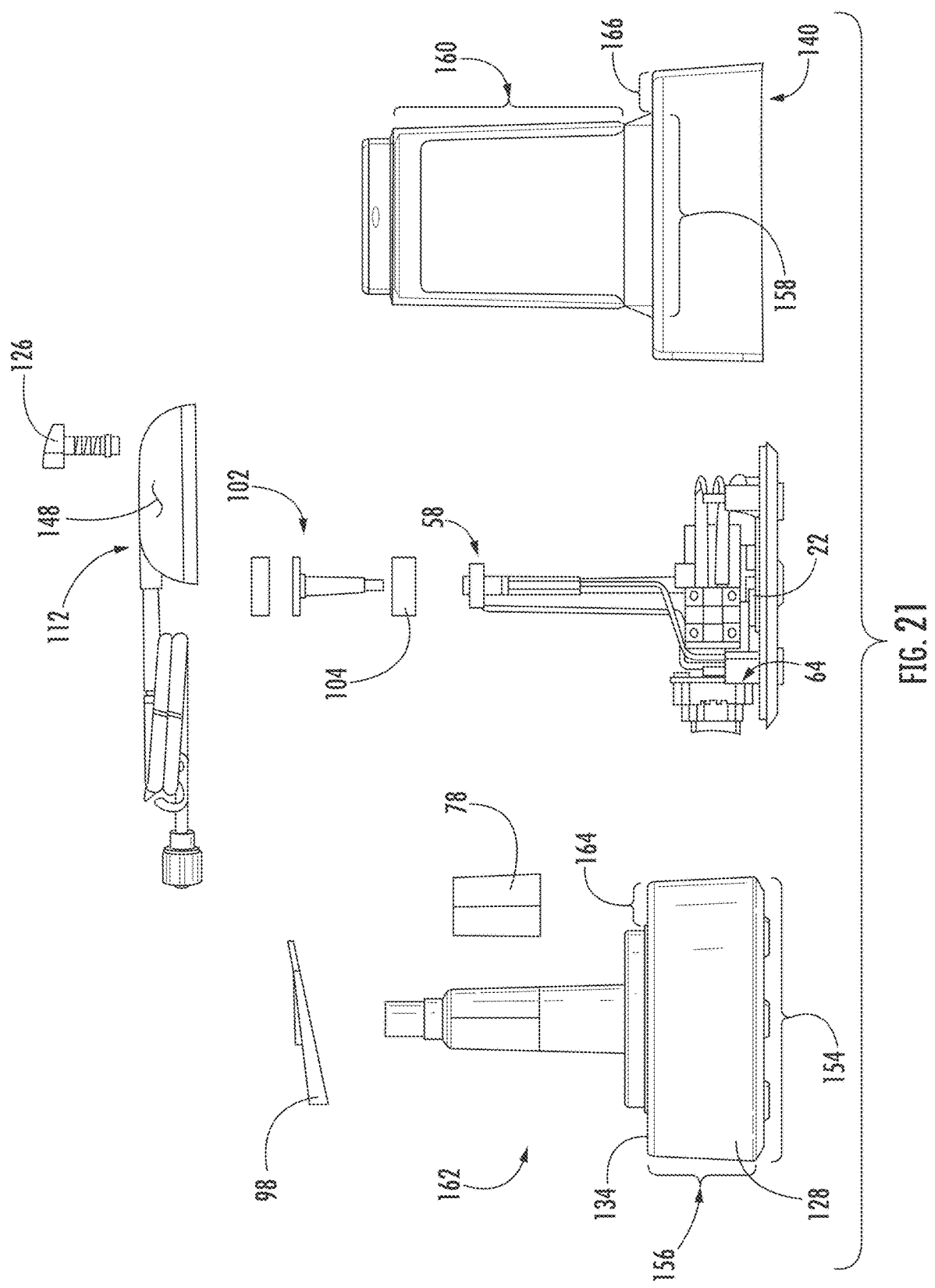
FIG. 21 is a left isometric exploded view of an embodiment of the disposable integrated aspiration pump and fluid collection device as described in the disclosure to illustrate the components as assembled.

FIG. 21 shows an embodiment wherein, the base sidewall 128 may be cylindrical and include a base width 154 and a base sidewall height 156. Also, the main cylindrical portion 142 of the canister housing 140 has a main cylindrical portion width 158 and height 160. The base width 154 is wider than the main cylindrical portion width 158. The base sidewall height 156 is less than the main cylindrical portion height 160.

An embodiment of the invention as shown in FIG. 20 may include the base sidewall 128, base top wall 130 and the column 34 as a unitary molded component 162. An outer perimeter portion 164 of the base top wall 130 is generally flat and void of the first ribbed pattern 136. The canister housing 140 may include an annular shelf 166 extending radially outward from the open bottom end 146 of the main cylindrical portion 142. An area of the annular shelf 166 is located above the outer perimeter portion 164 of the base top wall 130, and a skirt 168 extends downward from the annular shelf 166 of the canister housing 140. The skirt 168 is in an opposed facing relationship with the base sidewall 128. The base sidewall 128 includes at least one opening 170 for access to a power switch 172 and viewing of the pressure display 110, the power switch 172 and the display are located in the base compartment 20 with the skirt 168 having an aperture 174 to be generally aligned with the power switch 172.

Figure 4:
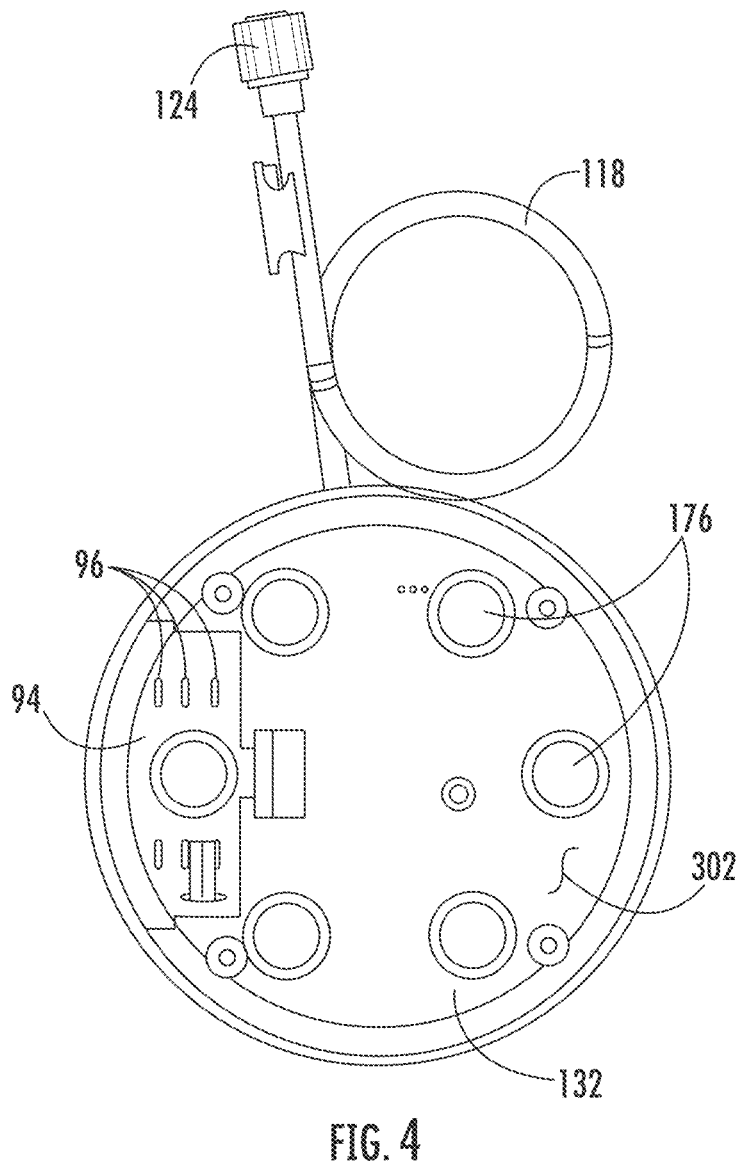
FIG. 4 is a bottom view of an embodiment of the disposable integrated aspiration pump and fluid collection device described in the disclosure.

In an embodiment of the invention the base bottom wall 132 is a separate component from the base 18, and includes the battery door 94 for gaining access to the battery compartment 66. The base bottom wall 132 supports the pump 22, the controller 56, the printed circuit board, the pressure transducer 108, the audible alarm 60, the power switch 172 and the pressure display 110 (specifically a segment light bar). The vent 96 in fluid communication with the base compartment 20 may also be a part of the base bottom wall 132. As illustrated in FIG. 4, a lower surface 302 of the base bottom wall 132 has low profile legs 176 to raise the lower surface 302 of the base bottom wall 132 and provide unobstructed flow for the vent 96. The printed circuit board 64 (PCB) aids in reducing the space needed to couple the controller 56 to the associated elements controlled by the controller 56. This allows the device 12 to remain compact, while also reducing the need for various connecting wires to the individual elements.

The low profile legs 176 are configured to elevate the device 12 above the environment surface during operation. The height of the low profile legs 176 may be between 0.140" to 0.180" so as to maintain a low center of gravity to improve stability. This elevation may improve the traction and stability of the device 12 when resting on the environment surface and also to allow improved venting of the positive pressure created by the pump 22 by increasing the volume of air being expressed through the vent. The base bottom wall 132 and low profile legs 176 may be made from any rigid material structurally capable of supporting the device 12. Suitable rigid materials may include plastics, metals, composites, or other natural and artificial materials which are commercially available. The low profile legs 176 may have an additional coating or be made from a material providing increased friction to reduce movement during operation. The low profile legs 176 may additionally be an integral portion of the base bottom wall 132 or base 18 to reduce the need for additional components.

Figure 16:
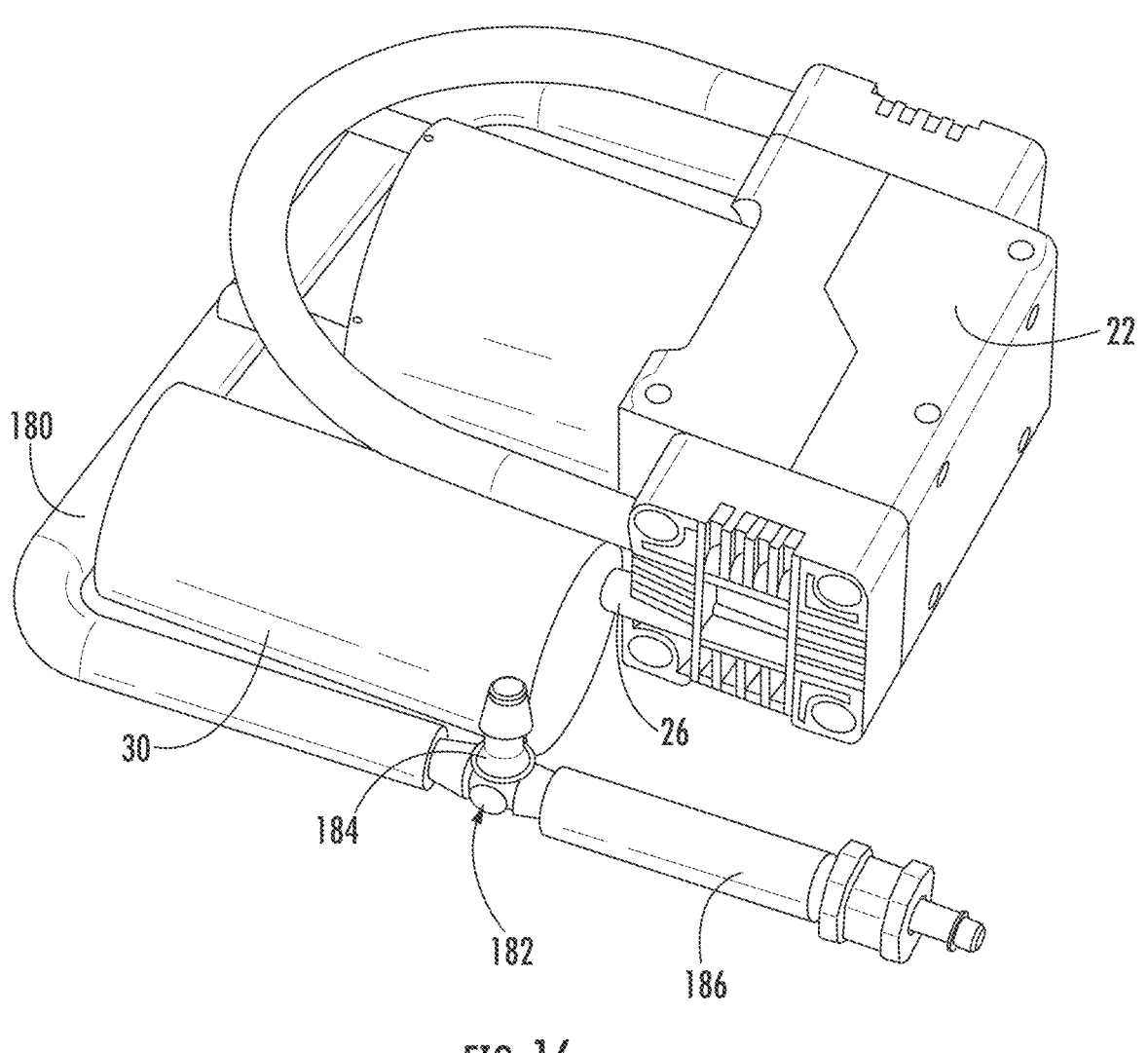
FIG. 16 is a top right isometric view of an embodiment of the pump, pump intake tube, mid-section, tap, mid-section tube as described in the disclosure.
Figure 17:
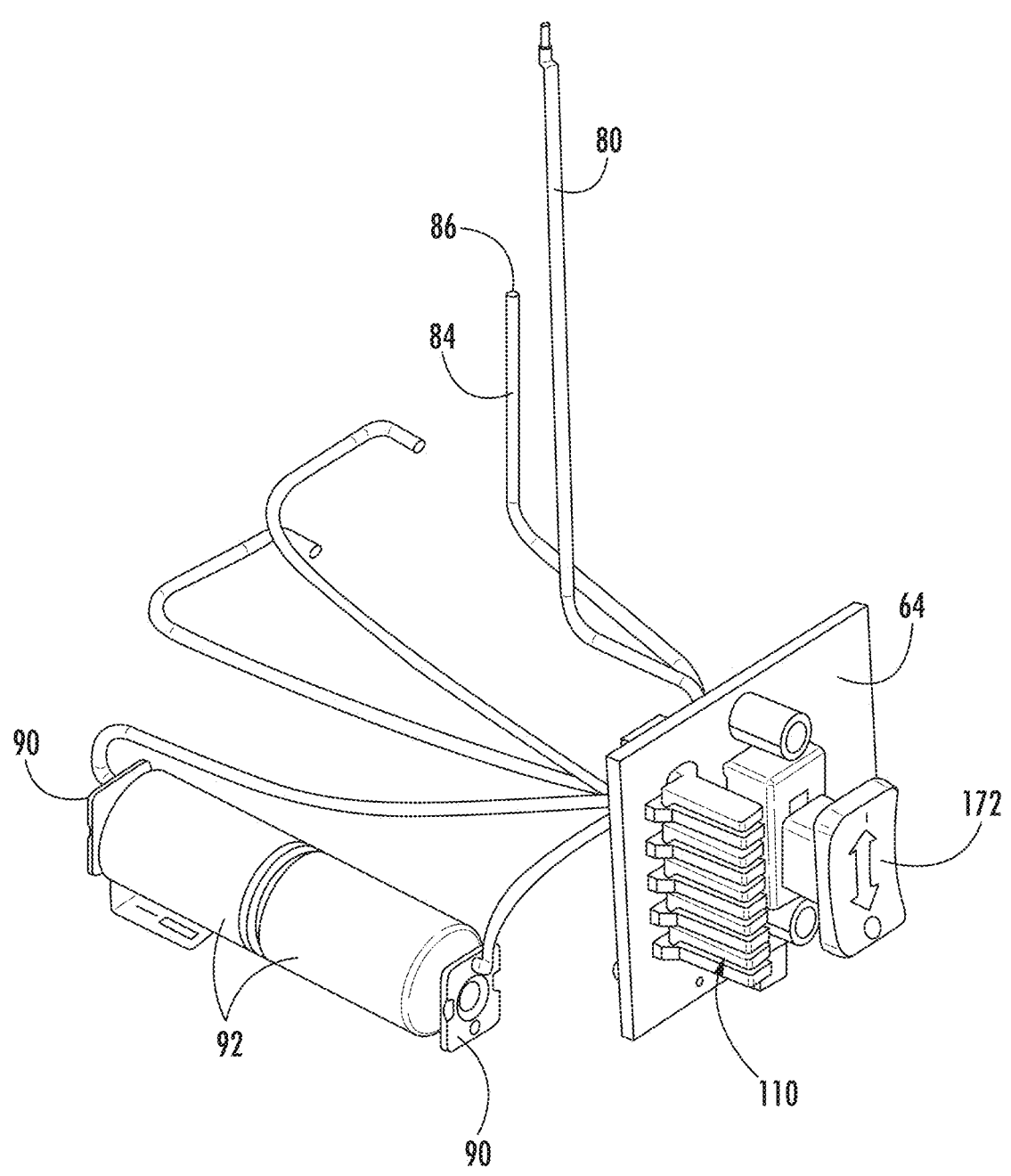
FIG. 17 is a top right isometric view of an embodiment of the batteries and PCB board to illustrate the electronically coupled layout of the components as described in the disclosure.
Figure 18:
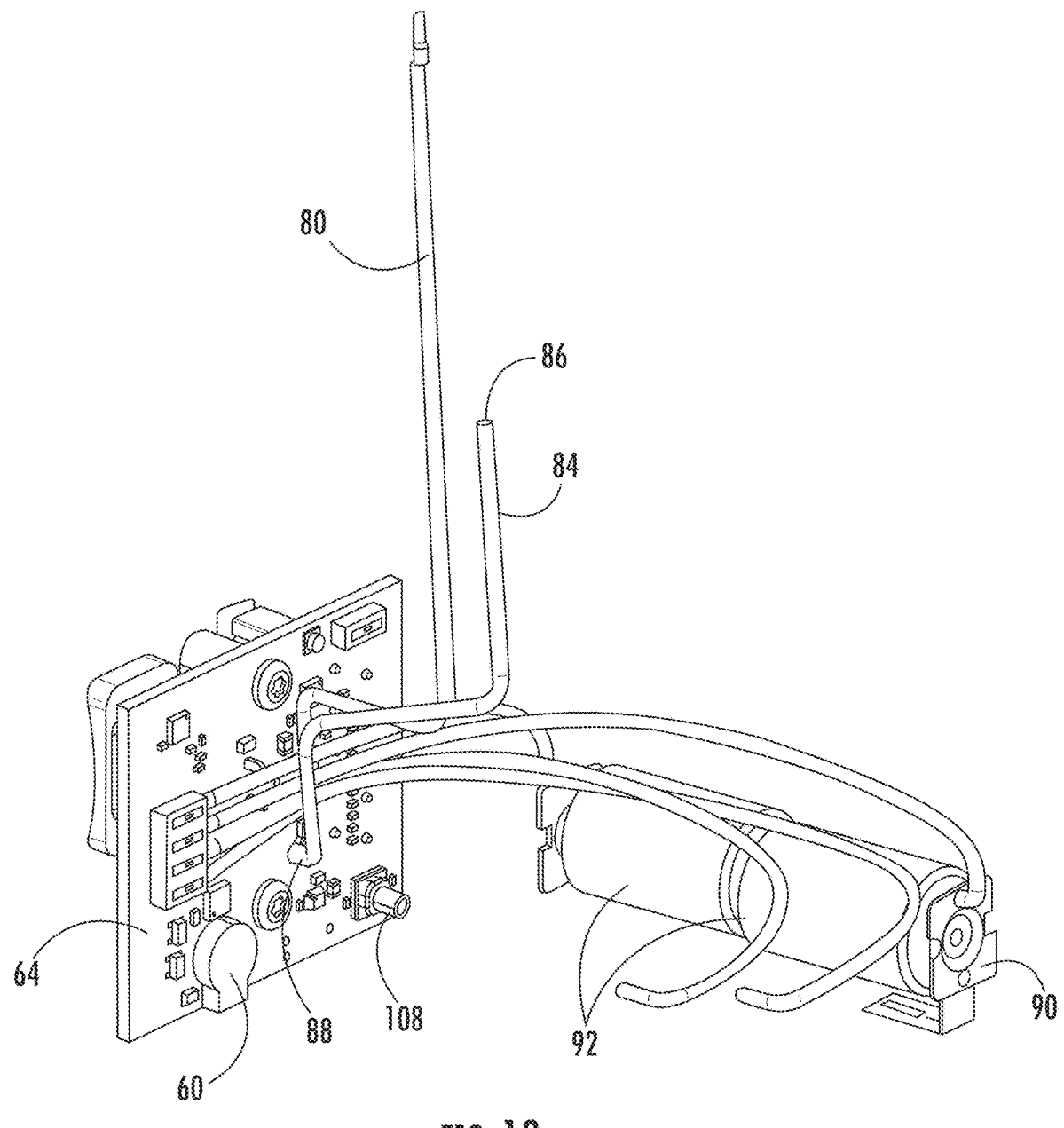
FIG. 18 is a rear left isometric view an embodiment of the batteries and PCB board to illustrate the electronically coupled layout of the components as described in the disclosure.

In an embodiment of the invention, the manifold 42 includes the generally disc shaped portion 46 which has the lower surface 48 which contains the inlets 44 facing in a downward direction. The manifold 42 includes a manifold tube portion 178 extending downward into the column 34 being in fluid communication with the second end of the suction tube. The first end 52 of the suction tube 50 is in fluid communication with a mid-section 182 which has a tap 184 configured to attach to a pump intake tube 180 and a mid-section tube 186. FIG. 16 illustrates the present embodiment's layout for the pump intake tube 180, mid-section 182, tap 184 and mid-section tube 186. The pump intake tube 180 is coupled to the intake port 24 of the pump 22. The mid-section tube 186 is coupled to the pressure transducer 108. Additionally, the float 104 is generally disc shaped and has a cylindrical bore 188 and an upper surface 190, wherein the column 34 extends through the cylindrical bore 188. The float 104 has a low fluid level position 192 and the shut-off level position 194, wherein in the shut-off level position 194, the upper surface 190 of the float 104 engages the inlets 44 and closes off the fluid communication between the inlets 44 and the fluid collection compartment 32. The float 104 moves between the low fluid level position 192, illustrated in FIG. 11, and the shut-off level position 194, illustrated in FIG. 10.

A Disposable Integrated Thrombectomy and Aspiration Apparatus

The disposable integrated thrombectomy and aspiration apparatus 14 for breaking up and aspirating thrombus or other obstructive material in a lumen of a vascular graft or vessel is removably coupled to the disposable integrated aspiration pump and fluid collection device 12. The apparatus 14 includes the following major components: a maceration wire 196, a motor 198 operatively connected to the maceration wire 196, and an aspiration pathway 200.

The maceration wire 196 extends in an axial direction and is configured to macerate the thrombus when rotated about a linear axis 202. The maceration wire 196 has a first arcuate region 204 extending in a first direction transverse to the axial direction and a second arcuate region 206 spaced in the axial direction from the first arcuate region 204 and extending in a second direction transverse to the axial direction. The first 204 and second 206 arcuate regions are positioned near a terminating end 208 of the maceration wire 196. The maceration wire 196 may comprise a variety of layers and segments with these layers and segments being used to provide the flexibility and shape required for the above features.

Figures 25, 26:
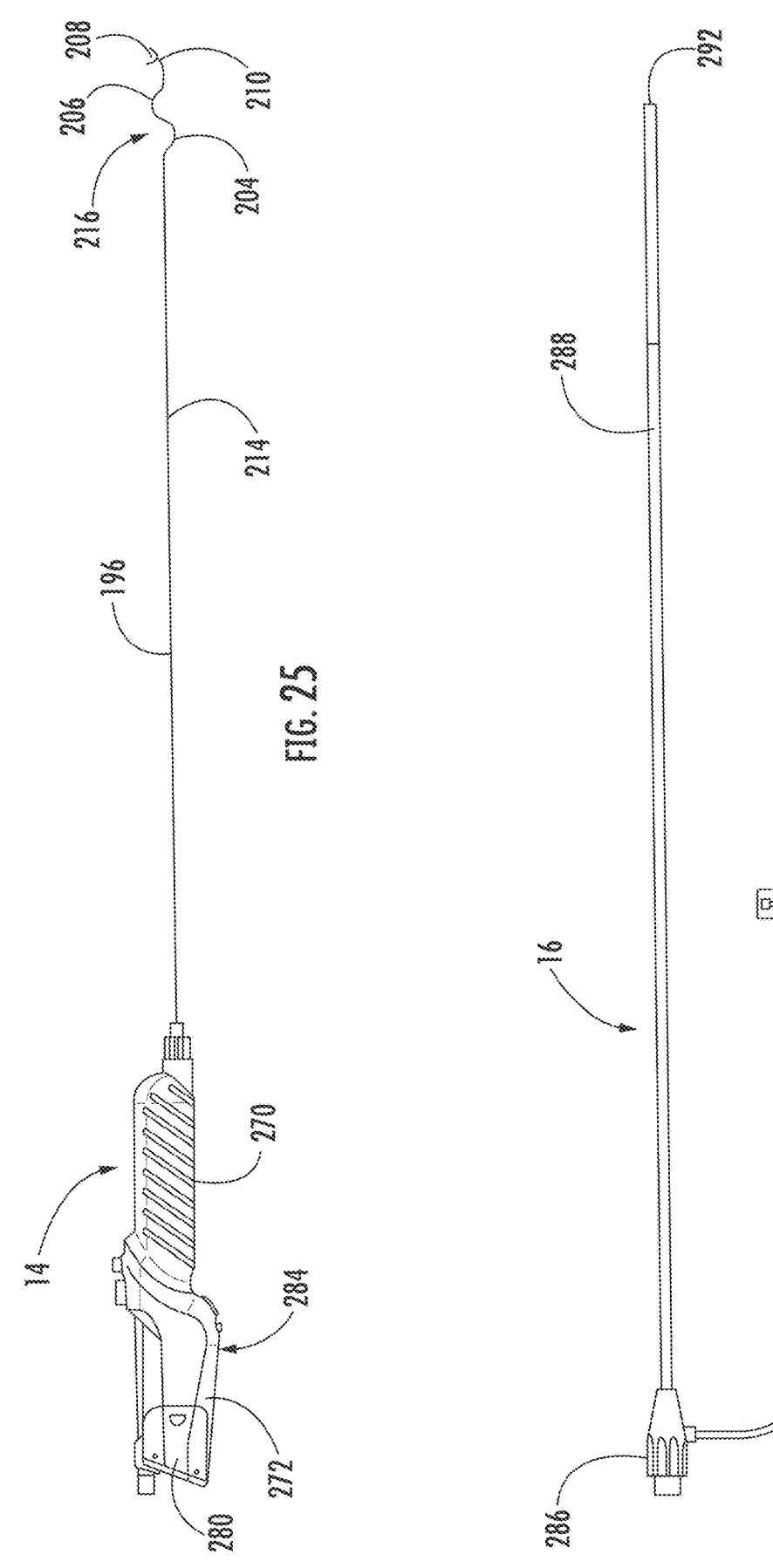
FIG. 25 is a right side view of an embodiment of the disposable integrated thrombectomy and aspiration apparatus without the catheter as described in the disclosure.
FIG. 26 is a right side view of an embodiment of the catheter as described in the disclosure.

In the present embodiment, the maceration wire 196 includes a tip 210 at the terminating end 208 of the maceration wire 196 as illustrated in FIG. 25. The tip 210 is configured to blunt the terminating end 208 to reduce trauma to the patient. The maceration wire 196 includes a coil core 212, a coil casing 214, and a terminating end cover 216 all designed to allow the maceration wire 196 to be flexible enough to have the first 204 and second 206 arcuate regions when deployed with the terminating end cover 216 providing a layer of protection between the coil casing 214 and the lumen of the patient.

The motor 198 is operatively connected to the maceration wire 196 opposite the terminating end 208 so as to rotate the macerating wire about the linear axis 202 such that the first arcuate region 204 and the second arcuate region 206 break up the thrombus or other obstructive material in the lumen. The motor 198 may be any commercially available motor suitable to the task of rotating the maceration wire 196 during operation. The motor 198 may be attached to the maceration wire 196 by any means capable of permanently securing the maceration wire 196 in place and maintaining that connection during operation whereby the wire will rotate when the motor 198 is actuated. Commercially available means may include one or more mechanical clamping, fusing, fastening, compressing sheaths or other suitable connection means. In the present embodiment a microtube 218 is permanently crimped to the maceration wire 196 opposite the terminating end 208 and attached to a drive shaft 220 of the motor 198 via a flexible coupler 222 which fixes the maceration wire 196 to rotate along with the drive shaft 220.

Figures 23, 24:
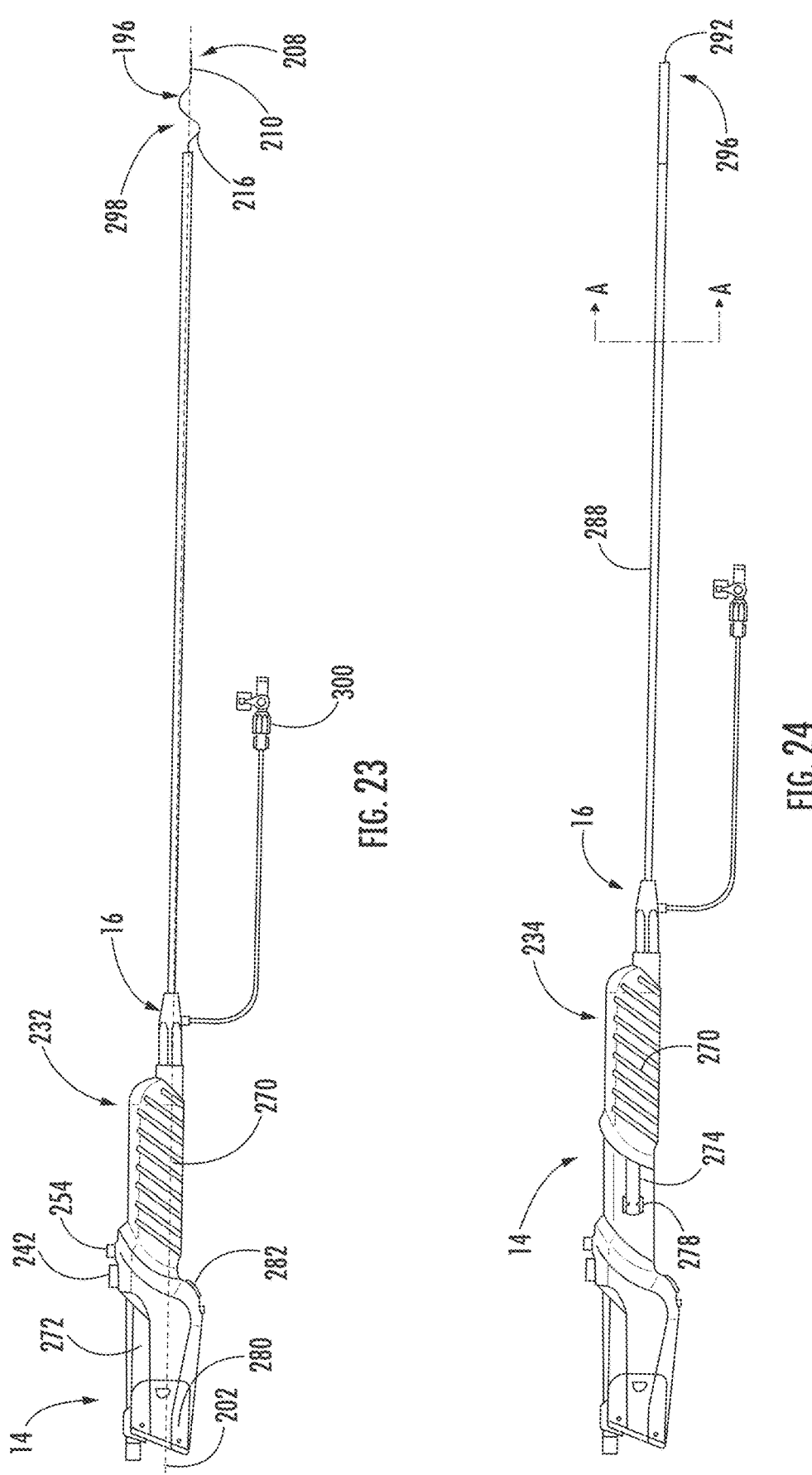
FIG. 23 is a right side view of an embodiment of the disposable integrated thrombectomy and aspiration apparatus and catheter in the deployed position as described in the disclosure.
FIG. 24 is a right side view of an embodiment of the disposable integrated thrombectomy and aspiration apparatus and catheter in the retracted position as described in the disclosure.

The aspiration pathway 200 extends in the axial direction between a catheter connection port 224 and an aspiration pump connection port 226 and has an interior surface 228. The catheter connection port 224 is configured to removably couple the catheter 16 to the apparatus 14 and the aspiration pump connection port 226 is configured to removably couple the apparatus 14 to the device 12 described above. Figure A-A illustrates how at least a portion of the aspiration pathway 200 includes an annular portion 230 defined as the boundary between the interior surface 228 of the aspiration pathway 200 and the maceration wire 196 whereby the macerated particulate may be aspirated from the patient. At least a portion of the interior surface 228 is slidable in relation to the maceration wire 196 when that portion is moved between a deployed position 232 and a retracted position 234. FIG. 23 Illustrates the apparatus 14 in the deployed position 232, and FIG. 24 illustrates the apparatus 14 in the retracted position 234. The maceration wire 196 extends through the catheter connection port 224 and into the catheter 16 when the catheter 16 is coupled to the apparatus 14.

The aspiration pathway 200 has an extraction portion 236 whereby the macerated particulate may be diverted from the annular portion 230 at a diversion point 238 positioned between the aspiration pump connection port 226 and the catheter connection port 224. The aspiration pathway 200 is further defined in part by an internal surface 240 of the extraction portion 236.

A variable flow control valve 242 may be located in the aspiration pathway 200 and configured to operate between a fully open condition 244 and a fully closed condition 246 whereby the user controls the amount of vacuum pressure passing through the aspiration pathway 200 by adjusting the variably flow control valve to the fully open condition 244, to the fully closed condition 246, or to position between the fully open 244 and the fully closed 246 conditions. In the present embodiment the aspiration valve is positioned in the extraction portion 236 nearer the aspiration pump connection port 226 than the diversion point 238.

The variable flow control valve 242 in the present embodiment comprises a plunger 248 which is biased 250 upwardly in the fully closed condition 246 with an aspiration shaft 252 extending from the plunger 248 configured to allow the user to manually press the plunger 248 downwardly and out of the aspiration pathway 200 to engage the fully open condition 244. The variable flow control valve 242 may comprise any method capable of controlling aspiration through the aspiration pathway 200, this includes all types of mechanical valves capable of opening and closing access through the aspiration pathway 200. The benefit to the present embodiment is that the user can manually control the aspiration between the fully open 244 and fully closed 246 conditions as desired for the specific procedure. This variable flow control valve 242 further improves user operability by not requiring the user to use the aspiration pump device 12 as the sole means of starting and stopping aspiration during the procedure. When not required, the variable flow control valve 242 can be placed in the fully closed position while the aspiration pump device 12 is operating. The variable flow control valve 242 saves time and improves vacuum pressure control by allowing control on the apparatus 14.

An injection port 254 may also be included as a part of the aspiration pathway 200, whereby the injection port 254 allows injectable solutions to enter the aspiration pathway 200. By allowing access to the aspiration pathway 200 the user can introduce the injectable solutions into the lumen without removing the present invention from the patient's body to save time and reduce trauma to the patient. Examples of injectable solutions include contrast medium to improve visibility of the affected area and treating chemicals which may aid in the maceration of the obstruction. The injection port 254 may be any commercially available one-way port or valve which allows for a sterile introduction without compromising the seal required by the aspiration pathway 200. During introduction, the variable flow control valve 242 needs to be in the fully closed condition 246 to prevent the injectable solution from being aspirated into the aspiration pump device 12.

Figures 27, 28:
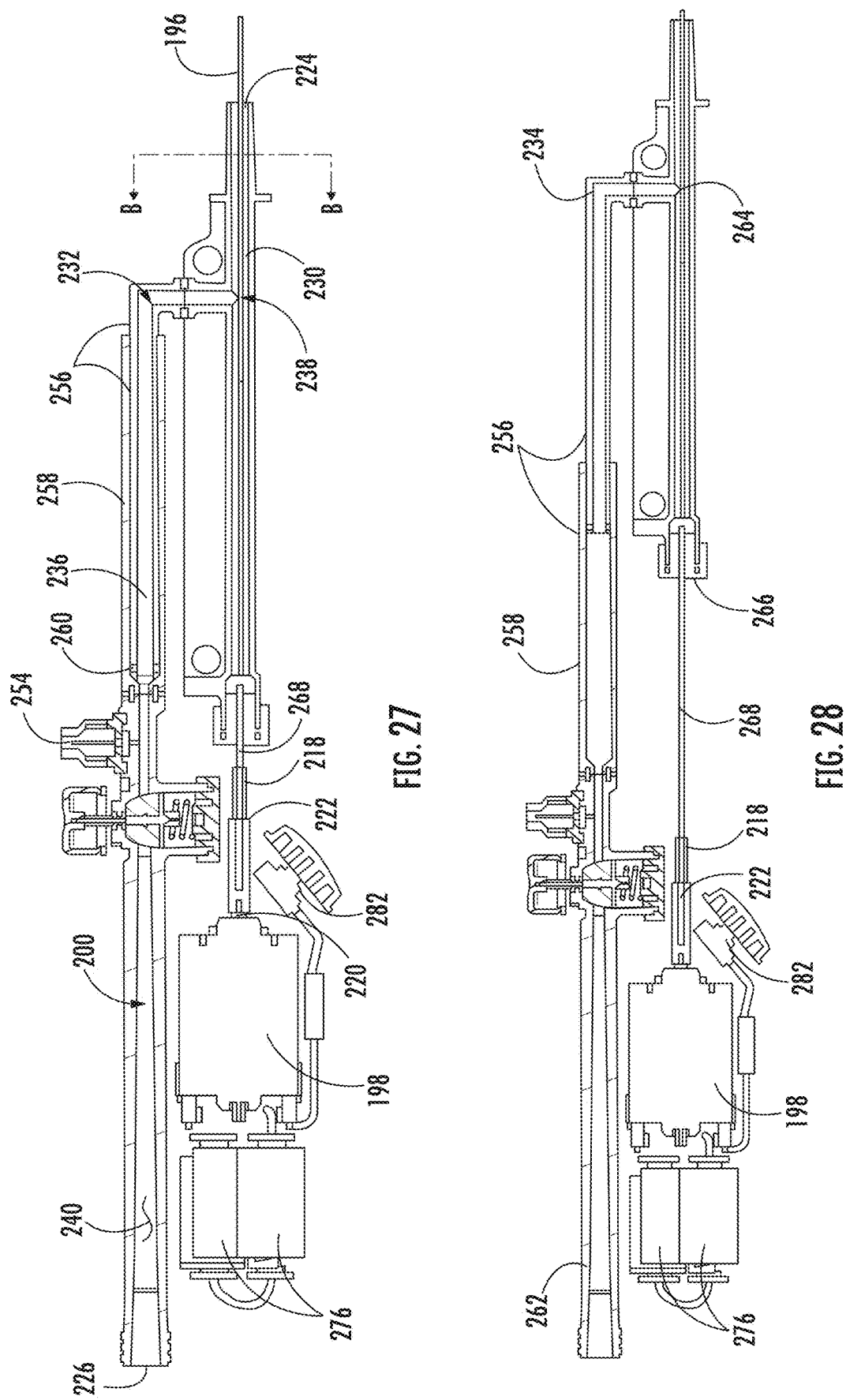
FIG. 27 is a right side section view of an embodiment of the disposable integrated thrombectomy and aspiration apparatus without the housing to show the internal features in the deployed position as described in the disclosure.
FIG. 28 is a right side section view of an embodiment of the disposable integrated thrombectomy and aspiration apparatus without the housing to show the internal features in the retracted position as described in the disclosure.
Figure 35:
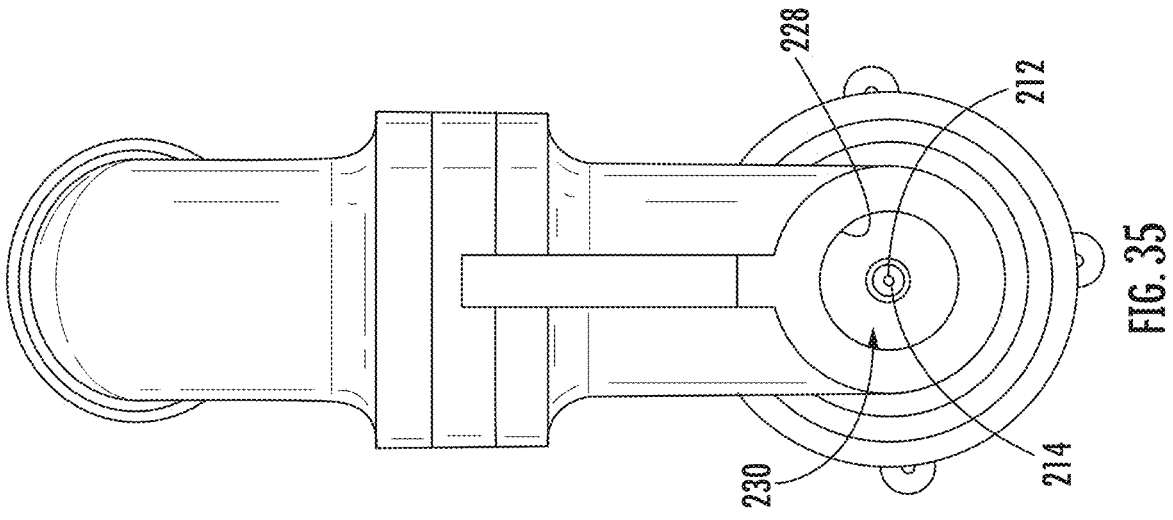
FIG. 35 is a cross-section view, taken along line B-B of FIG. 27, of the second section of the interface to illustrate the annular portion of the aspiration pathway and internal components of the maceration wire.
Figure 34:
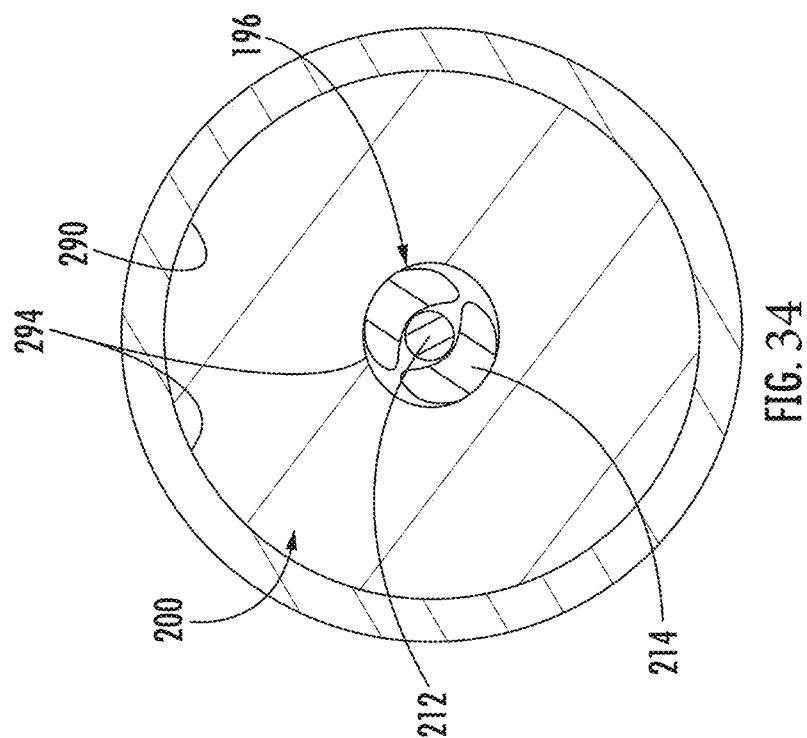
FIG. 34 is a cross-section view, taken along line A-A of FIG. 24, of the catheter and maceration wire to illustrate the catheter annular portion of the aspiration pathway and internal components of the maceration wire.
Figures 29, 30:
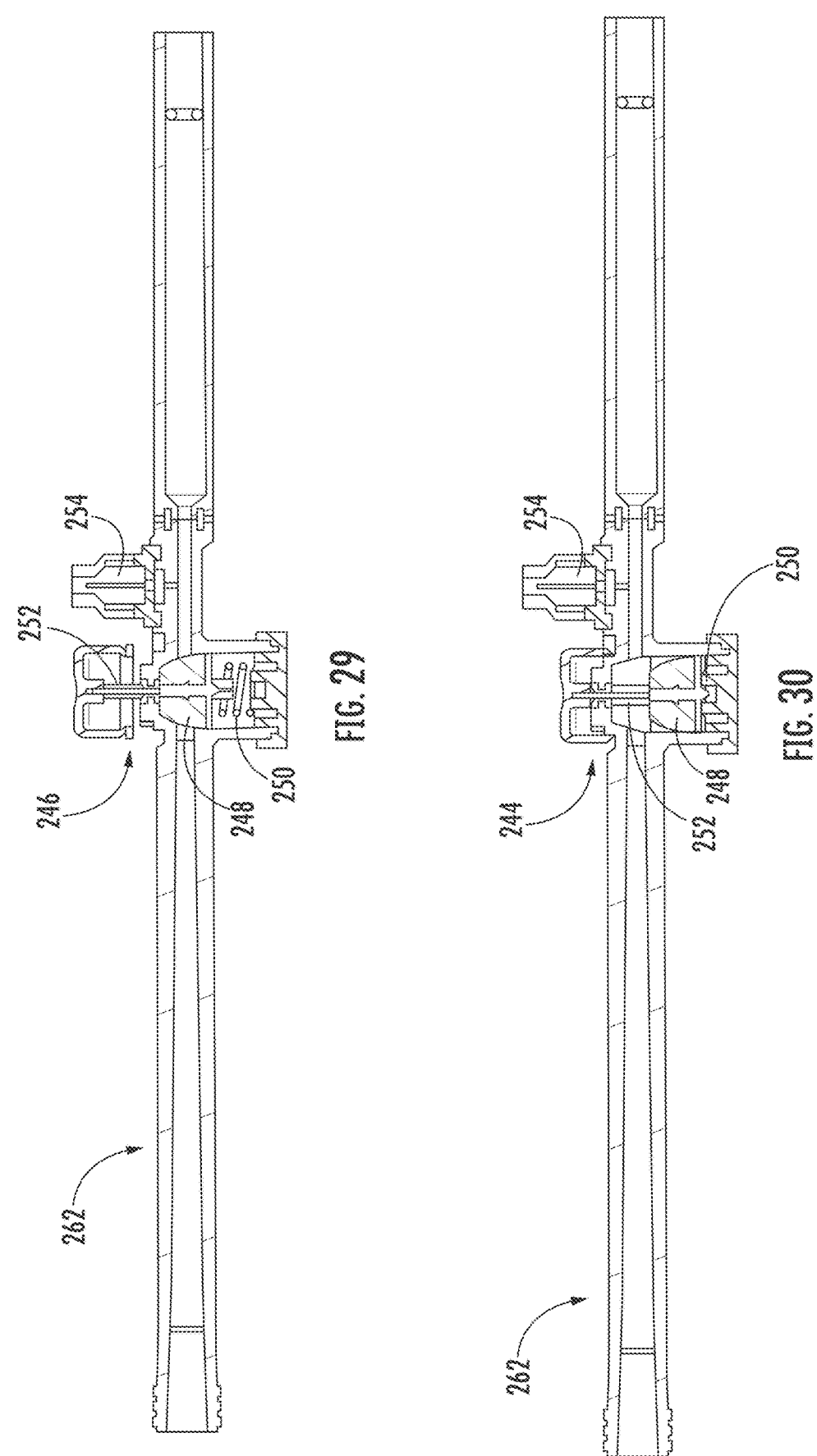
FIG. 29 is a right side section view of an embodiment of the first section of the interface illustrating the variable flow control valve in the fully closed condition as described in the disclosure.
FIG. 30 is a right side section view of an embodiment of the first section of the interface illustrating the variable flow control valve in the fully open condition as described in the disclosure.
Figure 31:
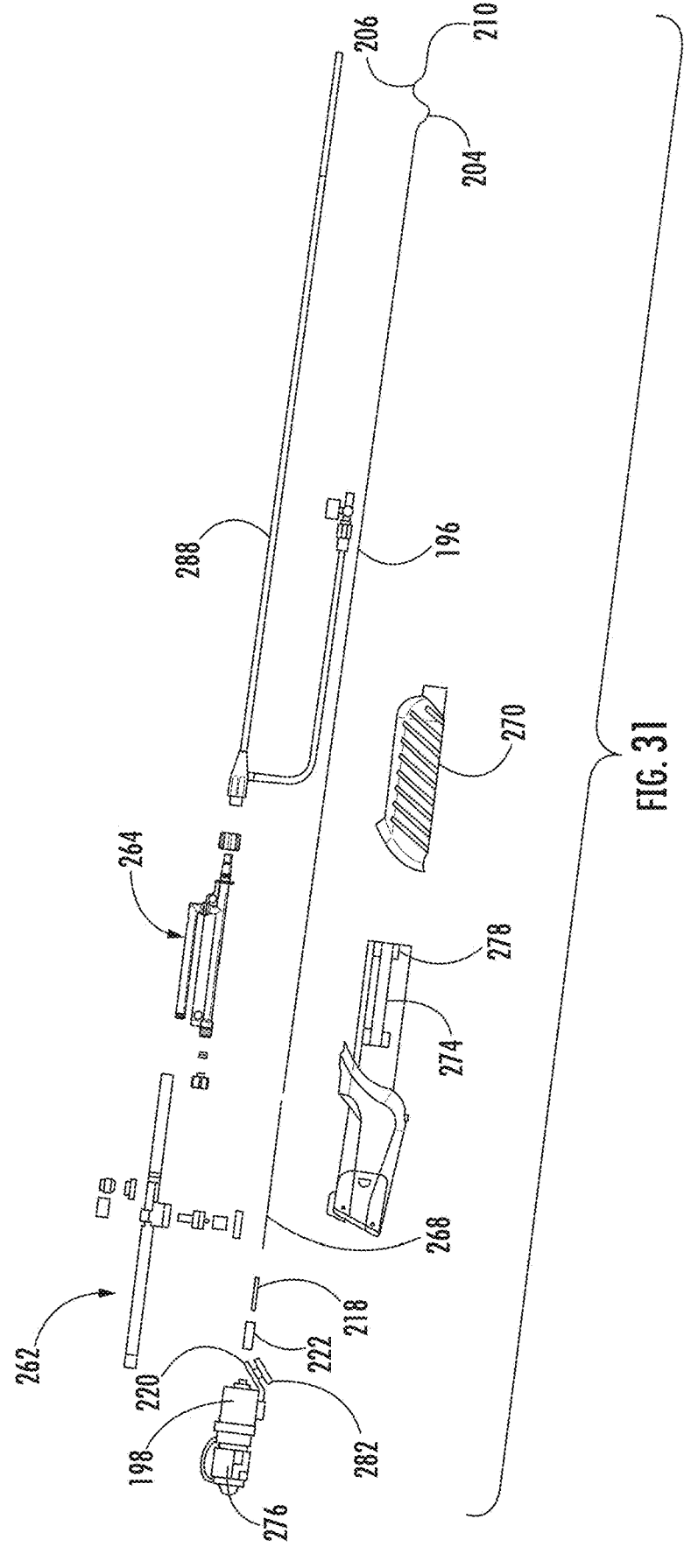
FIG. 31 is a top right isometric exploded view of an embodiment of the disposable integrated thrombectomy and aspiration apparatus to illustrate the orientation and assembly components of the invention as described in the disclosure.
Figure 32:
FIG. 32 is a right side exploded view of an embodiment of the disposable integrated thrombectomy and aspiration apparatus to illustrate the orientation and assembly components of the invention as described in the disclosure.
Figure 33:
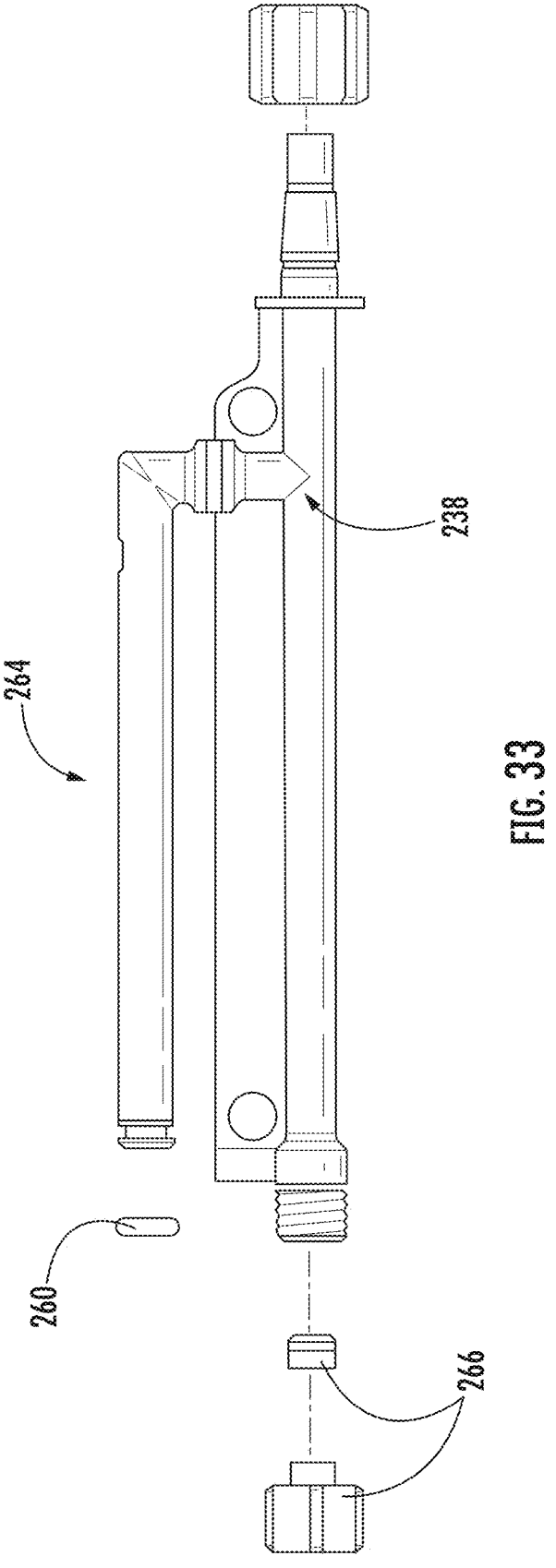
FIG. 33 is a right side exploded view of an embodiment of the second section of the interface as described in the disclosure.

The aspiration pathway 200 further includes an interface 256 which has a variable length and is fluidly operable with the aspiration pathway 200 when the aspiration pathway 200 is in the retracted position 234. At least a portion 258 of the interface 256 may be fluidly bypassed when the aspiration pathway 200 is in the deployed position 232 as shown in FIG. 27. One or more seals 260 in the aspiration pathway 200 maintain the vacuum pressure while the aspiration pathway 200 is moved between the deployed position 232 and the retracted position 234. The interior surface 228 and the catheter connection port 224 are slidable in relation to the maceration wire 196 along the axial direction when the aspiration pathway 200 moves between the deployed position 232 and the retracted position 234. The interface 256 allows the aspiration pathway 200 to extend while maintaining fluid operability. FIG. 23 illustrates that when in the deployed position 232 the terminating end 208 of the maceration wire 196 is extending beyond the catheter 16 and in the sinuous shape needed to macerate the walls of the lumen when rotated. When in the retracted position 234, the terminating end 208 of the maceration wire 196 is retracted into the catheter 16 and in a generally linear orientation to ease the maneuverability and reduce the risk of trauma while the catheter 16 and apparatus 14 are maneuvered into the desired location of the procedure.

FIG. 28 illustrates how in the present embodiment, the interface 256 comprises a first section 262 and a second section 264 which are telescopically coupled to and extending away from the first section 262. The first section 262, which includes the aspiration pump connection port 226, variable flow control valve 242, and injection port 254, is fixed in relation to the maceration wire 196. The second section 264, which includes the annular portion 230 and the catheter connection port 224 whereby the aspiration pathway 200 is extended when the second section 264 is in the retracted position 234, is slidably engaged with the maceration wire 196. The first 262 and second 264 sections are fluidly connected and sealed to maintain the vacuum pressure during operation. The sealing may be accomplished by any of a variety of commercially available means, including O-rings and valves which restrict access beyond a specific point. In the present embodiment, the first 262 and second 264 sections have an O-ring attached as the seal 260 to maintain contact between the telescopically coupled sections to prevent the pressure or macerated particulate from escaping the aspiration pathway 200 during movement between the deployed 232 and retracted 234 positions. Also, the second section 264 of the aspiration pathway 200 has a valve 266 which is in contact with a sheath 268 surrounding the maceration wire 196 adjacent to where the maceration wire 196 is attached to the motor 198 wherein the valve 266 and sheath are configured to seal the location where the maceration wire 196 passes through the annular portion 230 of the aspiration pathway 200 and to the motor 198. The maceration wire 196 is rotatably operable to maintain the function needed to macerate the obstruction, while the valve 266 and sheath 268 maintain the necessary seal.

A deployment control 270 is attached to the interface 256 and configured to move the aspiration pathway 200 between the deployed position 232 and the retracted position 234. The interface 256, a portion of the interior surface 228 of the aspiration pathway 200, and the catheter connection port 224 move with the deployment control 270. The deployment control 270 in the present embodiment is a handle, but a knob, a button, or any other graspable objects are intended to be alternative embodiments for the present invention. The deployment control 270 may be made from any rigid material, for example, structurally capable of withstanding multiple movements between the retracted 234 and deployed 232 positions as well as the stresses of the procedure. Suitable rigid materials may include plastics, metals, composites, or other natural and artificial materials which are commercially available.

A housing 272 containing at least a portion of the maceration wire 196, the motor 198, the aspiration pathway 200, one or more deployment tracks 274, a power source 276 and the above-mentioned features comprised in these individual parts may be included in the apparatus 14. The housing 272 provides the user a physical means to operate and manipulate the apparatus 14. The deployment tracks 274 define the pathway along which the deployment control 270 will move between the deployed position 232 and the retracted position 234. The deployment tracks 274 include a plurality of mechanical restraints 278 configured to removably secure the deployment control 270 in either the deployed position 232 or the retracted position 234. In the present embodiment of the invention the mechanical restraints 278 are flexible detents which deflect and removably secure to the deployment control 270 such that the user must apply a higher pressure to move the deployment control 270 and connected elements out of the deployed 232 or retracted 234 position.

The housing 272 shown in the present embodiment is constructed to be compact, disposable and with a unitary construction where possible to improve mobility, allow for sterilized pre-packaging and to reduce unnecessary assembly prior to use. The housing 272 may be a hand-grip size and shape whereby the user can actuate a maceration control 282 and manipulate the housing 272 with one hand. An example of such a hand-grip shape would be a pistol style grip found in similar apparatus. Disassembly of the housing 272 may be hampered by adhesives used in construction to reduce the temptation to re-sterilize and reuse the apparatus 14 in a subsequent procedure. The housing 272 may be made of any suitably rigid materials capable of withstanding the forces applied and sterility requirements of the procedure. Suitable materials may include plastics, metals, composites, or other natural and artificial materials which are commercially available.

The power source 276 may be rechargeable or disposable. Suitable power sources 276 may include dry cell, lithium-ion, nickel metal hydride or other commercially available batteries capable of powering the apparatus 14. In the present embodiment, lithium CR2 batteries are shown. The housing 272 may include a power source door 280 for removing and disposing of the power source 276 separate from the apparatus 14. By allowing the power source 276 to be removable the user can dispose of the components in the most efficient and safe manner available.

The maceration control 282 configured to actuate the motor 198 to rotate the maceration wire 196 is electronically coupled to the motor 198. The maceration control 282 is positioned on the housing 272 at a trigger finger position to allow the user to actuate the maceration control 282 without repositioning the user's hand during operation or positioning. The position of the maceration control 282 should be ergonomically located at an index finger position for the hand holding the apparatus 14. In the present invention, the maceration control 282 is positioned on a bottom edge 284 of the housing 272 such that the user can operate the maceration control 282 and variable flow control valve 242 while holding the apparatus 14 in a single hand. The maceration control 282 may be actuated by any commercially available means wherein the user can press or touch the maceration control 282 to actuate the motor 198.

Catheter

The catheter 16 is removably coupled to the catheter connection port 224 via a catheter coupler 286 and covers a portion of the maceration wire 196. The catheter 16 is configured to insert into the body of the patient and maneuver to the procedure location, and to extend the aspiration pathway 200 to the location site such that aspiration is possible around the maceration wire 196. FIG. 26 illustrates that the catheter 16 further includes a flexible sheath 288 extending distally in the axial direction away from the catheter coupler 286. The flexible sheath 288 has an inside surface 290 and a distal opening 292 positioned opposite of the catheter coupler 286. The inside surface 290 and the maceration wire 196 define a catheter annular portion 294 of the aspiration pathway 200 whereby the inside surface 290 is of sufficient size to allow the macerated particulate to be aspirated from the distal opening 292 toward the aspiration pump connection port 226 of the apparatus 14. The catheter 16 is slideably engaged with the maceration wire 196 and fixed to move in direct connection to the deployment control 270.

The flexible sheath 288 is relatively movable in the axial direction such that the terminating end 208 of the maceration wire 196 is near the distal opening 292 of the flexible sheath 288 wherein the maceration wire 196 has a first configuration 296 when the flexible sheath 288 is in the retracted position 234 and a second configuration 298 when the flexible sheath 288 is in the deployed position 232. In the first configuration 296, the wire is relatively linear when contained within the flexible sheath 288 and in the second configuration 298 the wire has a generally sinuous shape with the first 204 and second 206 arcuate regions extending away from the linear axis 202. The flexible sheath 288 may be made from any rigid material structurally capable of withstanding the pressure of the vacuum without collapsing to maintain the aspiration pathway 200 during operation. The material must also be flexible enough to navigate through the patient's body during the procedure. Suitable rigid materials may include plastics, metals, composites, or other natural and artificial materials which are commercially available. Since these materials are inserted into the patient's body, sterilization is essential, and the catheter 16 is intended to arrive sterile to the procedure area. There may be a variety of flexible sheath 288 sizes, shapes, materials, or other configurations which are specific to the procedure and patient's needs.

An auxiliary injection port 300 may be fluidly coupled to the catheter 16, whereby the auxiliary injection port 300 allows injectable solutions to enter the catheter annular portion 294 of the aspiration pathway 200. Similar to the injection port 254 described above, the variable flow control valve 242 should be in the fully closed position during introduction of the injectable solution. Examples of injectable solutions include contrast medium to improve visibility of the affected area and treating chemicals which may aid in the maceration of the obstruction. The auxiliary injection port 300 may be any commercially available one-way port or valve which allows for a sterile introduction without compromising the necessary seal required by the aspiration pathway 200.

The inside surface 290 of the flexible sheath 288 has a diameter between 5 F and 20 F (0.064" to 0.263") whereby the catheter annular portion 294 allows the maceration wire 196 to pass through the flexible sheath 288 and to rotate within the flexible sheath 288 while not obstructing the aspiration pathway 200.

Disposability and Sterilization

Medical devices are intended to save lives and improve the health and wellbeing of the patient, and to ensure this it is essential to reduce the risk of infection or contamination when operating equipment which will enter the patient's body. To this end it is a well-established practice to provide sterile equipment to the operation site and to make equipment disposable when feasible to reduce the chance of contamination from reuse. The invention 10 as presently embodied has several unique features and construction methods which reduce the cost of replacement and aid in safely disposing of the device 12, apparatus 14, and catheter 16.

Both the batteries 92 and power sources 276, for the apparatus 14 and the aspiration pump device 12, are removable to allow for disposal in the safest manner for the environment. Batteries 92 and power sources 276 often require unique disposal techniques to prevent environmental contamination or other dangerous conditions.

Similarly, medical waste requires specific procedural steps be taken to properly dispose of safely. The lid 112 for the aspiration pump device 12 is removable which allows the interior of the fluid collection compartment 32 to be accessible for collecting samples for testing or diagnosis or to empty the medical waste into a proper disposal container separate from the aspiration pump device 12. By allowing the waste to be removable, the aspiration pump device 12 can be disposed of in the most environmentally and economically available method.

Re-sterilization and reuse of the aspiration pump device 12 is discouraged by adding difficult to clean ribbed patterns 136 and 152 to the bottom of the fluid collection compartment 32 and lid 112. Additionally, inclusion of the fluid filter 98 will obstruct access for larger cleaning instruments into the fluid collection compartment 32 to reduce the chance of reuse. Permanent construction methods may also be used in the construction of the aspiration pump device 12 and apparatus 14 to not allow for separation of the pieces for replacement or re-sterilization. The housing 272 of the apparatus 14 may use adhesives or filling materials to fill any voids around the motor 198 or power supply to permanently attach the individual parts and prevent access to the motor 198 for replacement or to the aspiration pathway 200 for attempts at cleaning. The aspiration pathway's 200 configuration with the telescopically coupled interface 256 does not adequately allow for re-sterilization due to the lack of accessibility and interlocking construction. Reuse of the catheter 16 would be highly irresponsible due to the amount of contact the catheter 16 has with the patient, so disposability is nearly a requirement. The maceration wire 196 is also in direct contact with the patient and is permanently attached to the motor 198 which makes replacement impractical without permanently damaging the housing 272 of the apparatus 14.

Additionally, disposability allows for the components used to be chosen with performance taking priority over durability. By choosing the pump 22 and motor 198 that are highly effective but not designed for extended use or reuse, the equipment can reduce the costs often associated with large capital investment equipment which locks the buyer into larger costs and longer cost recuperation windows. Reusable equipment is also subject to repair costs and re-sterilization costs which may be difficult to estimate at the time of purchase.

The present invention is designed to be disposable, modular, sterile, and economical, by implementing a compact and unitary design along with permanent assembly methods to ensure the user and patient receive the best available operational capabilities while reducing economical costs.

In use, the individual components of the invention arrive to the procedure site in individually packaged and sterile units. Once opened and assembled the deployment control 270 of the apparatus 14 should be placed in the retracted position 234 which will put the maceration wire 196 in the first configuration 296 during positioning. The distal opening 292 of the flexible sheath 288 can be inserted into the patent and maneuvered to the site of the obstruction. The distal opening 292 is then moved through the obstruction and the deployment control 270 moved into the deployed position 232 which places the maceration wire 196 into the second configuration 298. The aspiration pump device 12 can be actuated when desired and the desired vacuum pressure can be obtained. The maceration control 282 may then be actuated to rotate the maceration wire 196 while the maceration wire 196 and apparatus 14 are moved backward through the obstruction to macerate the obstruction. Aspiration can be applied during the maceration whereby the macerated materials will then pass through the aspiration pathway 200 throughout the catheter 16 and apparatus 14 before depositing in the fluid collection compartment 32 of the device 12. The aspiration can continue with or without maceration until the macerated particulate has been removed or the aspiration pump device 12 has been filled.

Optionally, the user may introduce substances into the vessel prior to maceration by utilizing the injection port 254 or auxiliary injection port 300. Balloons and other surgical equipment may also be introduced prior to or after maceration by detaching and removing the apparatus 14 from the catheter 16 before inserting the equipment through the catheter 16 and flexible sheath 288. By allowing these additional operations to be accomplished without need for additional catheter 16 insertion and maneuvering, the patient is put through much less trauma and risk for injury. By adding aspiration to the prior art utilizing maceration wires 196, the present invention is able to provide an additional benefit without requiring separate equipment or disconnection from the apparatus 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A disposable integrated aspiration pump and fluid collection device comprising:

a base having a base compartment;

a pump located in said base compartment, said pump includes an intake port and an exhaust port;

a fluid collection compartment located above said base;

a column extends within said fluid collection compartment in substantially a vertical direction, said column includes a lower portion and an upper portion, said column having a cavity connected to said base compartment;

a manifold is located at said upper portion of said column, said manifold includes one or more inlets; and a suction tube includes a first end and a second end, said first end of said suction tube is in fluid communication with said intake port of said pump, said suction tube extends through said cavity of said column, and said second end of said suction tube is in fluid communication with said one or more inlets, wherein said manifold includes a generally disc shaped portion, said generally disc shape portion including a lower surface which includes said one or more inlets, whereby said one or more inlets face in a downward direction.

2. The disposable integrated aspiration pump and fluid collection device of claim 1, wherein said pump is rated to have a low flow rate and a high-vacuum capacity.

3. The disposable integrated aspiration pump and fluid collection device of claim 2, wherein said pump has a flow rate greater than 1.5 liters per minute (L/min) and a maximum vacuum between 5 inHg and absolute vacuum, wherein absolute vacuum is 0 inHg.

4. The disposable integrated aspiration pump and fluid collection device of claim 2, wherein said pump is a diaphragm pump.

5. The disposable integrated aspiration pump and fluid collection device of claim 1, further comprising a controller located in said base and battery contacts for receiving one or more batteries, said battery contacts couple said batteries to said controller, said base includes a door for removing and disposing of said batteries separate from said device, said base further includes a vent in fluid communication with said base compartment and ambient air.

6. The disposable integrated aspiration pump and fluid collection device of claim 1, further comprising a fluid filter located within said fluid collection compartment.

7. The disposable integrated aspiration pump and fluid collection device of claim 1, further comprising a controller located in said base, a fluid level sensor and an audible alarm, said fluid level sensor is located at a designated sensor elevation within said fluid collection compartment, said fluid level sensor is coupled to said controller, said controller includes a means to activate said audible alarm for a preset amount of time when said fluid level sensor detects fluid at said designated sensor elevation, and at an end of said preset amount of time, said controller shuts off said pump.

8. The disposable integrated aspiration pump and fluid collection device of claim 1, further comprising a float shut off mechanism, said float shut off mechanism includes a float located below said one or more inlets of said manifold, whereby when a level of fluid rises and raises said float to a designated maximum fluid elevation, said float will engage said one or more inlets and close off fluid communication between said one or more inlets and said fluid collection compartment.

9. The disposable integrated aspiration pump and fluid collection device of claim 1, further comprising a pressure transducer and a pressure display, said pressure transducer and said pressure display are coupled to a controller located in said base, said suction tube is in fluid communication with said pressure transducer, said controller includes a means of determining a pressure measured at said pressure transducer and displaying the measured pressure on said pressure display, said controller includes means for operating said pump to regulate the pressure.

10. The disposable integrated aspiration pump and fluid collection device of claim 9, wherein said pressure display consists of a segment bar display.

11. The disposable integrated aspiration pump and fluid collection device of claim 1, further comprising a suction port being in fluid communication with said fluid collection compartment, said suction port includes a catheter fitting for coupling to a catheter, whereby the catheter may be connected to another medical device.

12. A disposable integrated aspiration pump and fluid collection device comprising:

a base having a base compartment;

a pump located in said base compartment, said pump includes an intake port and an exhaust port;

a fluid collection compartment located above said base;

a column extends within said fluid collection compartment in substantially a vertical direction, said column includes a lower portion and an upper portion, said column having a cavity connected to said base compartment;

a manifold is located at said upper portion of said column, said manifold includes one or more inlets;

a suction tube includes a first end and a second end, said first end of said suction tube is in fluid communication with said intake port of said pump, said suction tube extends through said cavity of said column, and said second end of said suction tube is in fluid communication with said one or more inlets; and a controller located in said base, a fluid level sensor and an audible alarm, said fluid level sensor is located at a designated sensor elevation within said fluid collection compartment, said fluid level sensor is coupled to said controller, said controller includes a means to activate said audible alarm for a preset amount of time when said fluid level sensor detects fluid at said designated sensor elevation, and at said end of said preset amount of time, said controller shuts off said pump, wherein said cavity is in fluid communication with said base compartment, said cavity is closed off at said upper portion, said fluid level sensor includes a non-contact capacitance sensor, said column includes an inner and outer surface, said fluid level sensor including a strip of copper having a first and second end, said strip of copper is located on said inner surface of said column extending around a portion of a circumference of said inner surface and forming a gap between said first and second ends of said strip of copper, a hydrophobic film is located on at least a portion of said outer surface of said column, a sensor wire couples said strip of copper to said controller, a portion of said suction tube extending within said cavity of said column is covered by a shielding material, a shielding wire has a first end and a second end, said first end of said shielding wire is coupled to ground on said controller and said second end of said shielding wire is coupled to said shielding material.

13. A disposable integrated aspiration pump and fluid collection device comprising:
   a base having a base compartment;
   a pump located in said base compartment, said pump includes an intake port and an exhaust port;
   a fluid collection compartment located above said base;
   a column extends within said fluid collection compartment in substantially a vertical direction, said column includes a lower portion and an upper portion, said column having a cavity connected to said base compartment;
   a manifold is located at said upper portion of said column, said manifold includes one or more inlets;
   a suction tube includes a first end and a second end, said first end of said suction tube is in fluid communication with said intake port of said pump, said suction tube extends through said cavity of said column, and said second end of said suction tube is in fluid communication with said one or more inlets; and
   a lid closing off an open top end of said fluid collection compartment, said lid is removable to expose an interior of said fluid collection compartment, a manually operated pressure equilibration valve is secured to said fluid collection compartment and when operated equalizes a pressure in said fluid collection compartment to ambient pressure, and a suction port is in fluid communication with said fluid collection compartment, said suction port includes a catheter fitting for coupling to a connection catheter or other tube, said connection catheter fitting extends from said lid in a horizontal direction to provide a low profile, and including a connection catheter having a first end and a second end, said first end of said connection catheter being secured to said catheter fitting and said second end of said connection catheter having an aspiration coupling.

14. A disposable integrated aspiration pump and fluid collection device comprising:
   a base having a base compartment;
   a pump located in said base compartment, said pump includes an intake port and an exhaust port;
   a fluid collection compartment located above said base;
   a column extends within said fluid collection compartment in substantially a vertical direction, said column includes a lower portion and an upper portion, said column having a cavity connected to said base compartment;
   a manifold is located at said upper portion of said column, said manifold includes one or more inlets; and
   a suction tube includes a first end and a second end, said first end of said suction tube is in fluid communication with said intake port of said pump, said suction tube extends through said cavity of said column, and said second end of said suction tube is in fluid communication with said one or more inlets,
   wherein said base includes a base sidewall, a base top wall, and a base bottom wall, said base sidewall, base top wall and base bottom wall define said base compartment, said column extends vertically from said base top wall, said base top wall includes an upper surface surrounding said column, said upper surface of said base top wall includes a first ribbed pattern which rises above said upper surface, said column is generally cylindrical and includes the lower portion and the upper portion, said lower portion of said column has a tapered profile in the vertical direction, said lower portion of said column and said upper portion of said column are separated by a stepped portion, said upper portion includes a tapered profile in the vertical direction, said manifold is secured to said upper portion of said column.

15. The disposable integrated aspiration pump and fluid collection device of claim 14, further comprising a transparent canister housing, said canister housing includes a main cylindrical portion having an open top end and an open bottom end, said open bottom end of said canister housing is closed by said base, a removable lid seals said open top end, said lid includes an upper surface and a lower surface, said lower surface of said lid includes a second ribbed pattern which extends below said lower surface of said lid, wherein said main cylindrical portion of said canister housing, said lid, said upper surface, and said column of said base define said liquid compartment.

16. The disposable integrated aspiration pump and fluid collection device of claim 15, wherein said base sidewall is cylindrical and includes a base width and a base sidewall height, and said main cylindrical portion of said transparent canister housing has a main cylindrical portion width and height, said base width being wider than said main cylindrical portion width.

17. The disposable integrated aspiration pump and fluid collection device of claim 16, wherein said base sidewall, said base top wall and said column are a unitary molded component, an outer perimeter portion of said base top wall is generally flat and void of said first ribbed pattern, and said transparent canister housing includes an annular shelf extending radially outward from said open bottom end of said main cylindrical portion, an area of said annular shelf is located above said outer perimeter portion of said base top wall, and a skirt extends downward from said annular shelf of said transparent canister housing, said skirt is in opposed facing relationship with said base sidewall.

18. The disposable integrated aspiration pump and fluid collection device of claim 17, wherein said base sidewall includes at least one opening for access to a power switch and viewing of a display, said power switch and said display located in said base compartment, and said skirt includes an aperture to be generally aligned with said power switch.

19. The disposable integrated aspiration pump and fluid collection device of claim 17, wherein said base bottom wall is a separate component from said base, and said base bottom wall includes a battery door for gaining access to a battery compartment, said base bottom wall supports said pump, a controller, a printed circuit board, a pressure transducer, an audible alarm, a power switch and a segment light bar, a vent is in fluid communication with said base compartment, a lower surface of said base bottom wall includes low profile legs to raise said lower surface of said base bottom wall and provide unobstructed flow for said vent.

20. The disposable integrated aspiration pump and fluid collection device of claim 14, wherein a fluid filter is located on said column at said stepped portion.

21. A disposable integrated aspiration pump and fluid collection device comprising:
   a base having a base compartment;
   a pump located in said base compartment, said pump includes an intake port and an exhaust port;
   a fluid collection compartment located above said base;

a column extends within said fluid collection compartment in substantially a vertical direction, said column includes a lower portion and an upper portion, said column having a cavity connected to said base compartment;

a manifold is located at said upper portion of said column, said manifold includes one or more inlets;

a suction tube includes a first end and a second end, said first end of said suction tube is in fluid communication with said intake port of said pump, said suction tube extends through said cavity of said column, and said second end of said suction tube is in fluid communication with said one or more inlets; and a float shut off mechanism, said float shut off mechanism includes a float located below said one or more inlets of said manifold, whereby when a level of fluid rises and raises said float to a designated maximum fluid elevation, said float will engage said one or more inlets and close off fluid communication between said one or more inlets and said fluid collection compartment, wherein said manifold includes a generally disc shaped portion, said generally disc shape portion including a lower surface which includes said one or more inlets, whereby said one or more inlets face in a downward direction, said manifold includes a manifold tube portion which extends downward into said column being in fluid communication with said second end of said suction tube, said first end of said suction tube being in fluid communication with a mid-section having a tap configured to attach to a pump intake tube and a mid-section tube, said pump intake tube being coupled to said intake port of said pump, said mid-section tube being coupled to a pressure transducer, and wherein said float is generally disc shape having a cylindrical bore and an upper surface, wherein said column extends through said cylindrical bore of said float, said float having a low fluid level position and a shut-off level position, wherein in said shut-off level position, said upper surface of said float engages said one or more inlets and close off the fluid communication between said one or more inlets and said fluid collection compartment.

22. A disposable integrated aspiration pump and fluid collection device comprising:

a base having a base compartment;

a pump located in said base compartment, said pump includes an intake port and an exhaust port;

a fluid collection compartment located above said base;

a column extends within said fluid collection compartment in substantially a vertical direction, said column includes a lower portion and an upper portion, said column having a cavity connected to said base compartment;

a manifold is located at said upper portion of said column, said manifold includes one or more inlets;

a suction tube includes a first end and a second end, said first end of said suction tube is in fluid communication with said intake port of said pump, said suction tube extends through said cavity of said column, and said second end of said suction tube is in fluid communication with said one or more inlets;

wherein said manifold includes a generally disc shaped portion, said generally disc shape portion including a lower surface which includes said one or more inlets, whereby said one or more inlets face in a downward direction; and a pressure transducer and a pressure display, said pressure transducer and said pressure display are coupled to a controller located in said base, said suction tube is in fluid communication with said pressure transducer, said controller includes a means of determining a pressure measured at said pressure transducer and displaying the measured pressure on said pressure display, said controller includes means for operating said pump to regulate the pressure, wherein said controller includes means for regulating the pressure to a preset maximum vacuum, and means for displaying a measured vacuum.

23. A disposable integrated thrombectomy and aspiration apparatus for breaking up and aspirating thrombus or other obstructive material in a lumen of a vascular graft or vessel, said apparatus comprising a maceration wire extending in an axial direction;

a motor operatively connected to said maceration wire;

an aspiration pathway extending between a catheter connection port and an aspiration pump connection port and including an interior surface, at least a portion of said aspiration pathway including an annular portion defined as a boundary between said interior surface of said aspiration pathway and said maceration wire whereby macerated particulate may be aspirated from the patient, at least a portion of said interior surface being slidable in relation to said maceration wire when said portion of said interior surface is moved between a deployed position and a retracted position, said maceration wire extending through said catheter connection port; and a housing having the aspiration pump connection port at a proximal end of the housing and the catheter connection port at a distal end of the housing, wherein the aspiration pathway extends in an axial direction between the catheter connection port and the aspiration pump connection port, wherein said aspiration pathway further includes an interface having a variable length and being fluidly operable with said aspiration pathway when said aspiration pathway is in said retracted position, at least a portion of said interface being fluidly bypassable when said aspiration pathway is in said deployed position, one or more seals in said aspiration pathway maintain a vacuum pressure while said aspiration pathway is moved between said deployed position and said retracted position, a portion of said interior surface and said catheter connection port being slidable in relation to said maceration wire along said axial direction when said aspiration pathway moves between said deployed position and said retracted position.

24. The disposable integrated thrombectomy and aspiration apparatus of claim 23, wherein said aspiration pathway includes an extraction portion whereby the macerated particulate may be diverted from said annular portion at a diversion point positioned between said aspiration pump connection port and said catheter connection port, said aspiration pathway being further defined in part by an internal surface of said extraction portion.

25. The disposable integrated thrombectomy and aspiration apparatus of claim 23, wherein said aspiration pathway includes a variable flow control valve having a fully open condition and a fully closed condition whereby a user can control an amount of vacuum pressure passing through said aspiration pathway by adjusting said variable flow control valve to said fully open condition, to said fully closed condition, or to a position between said fully open and said fully closed conditions.

26. The disposable integrated thrombectomy and aspiration apparatus of claim 23, wherein said aspiration pathway includes an injection port, whereby said injection port allows injectable solutions to enter said aspiration pathway.

27. The disposable integrated thrombectomy and aspiration apparatus of claim 23, wherein said interface comprises a first section and a second section being telescopically coupled to and extending away from said first section, said first section including said aspiration pump connection port and being fixed in relation to said maceration wire, said second section including said annular portion and said catheter connection port whereby said aspiration pathway is extended when said second section is in said retracted position, said second section being slidably engaged with said maceration wire, said first and second sections being fluidly connected and sealed to maintain the vacuum pressure during operation.

28. The disposable integrated thrombectomy and aspiration apparatus of claim 23, further comprising a deployment control configured to move said aspiration pathway between said deployed position and said retracted position, whereby said interface, a portion of said interior surface of said aspiration pathway, and said catheter connection port move with said deployment control.

29. The disposable integrated thrombectomy and aspiration apparatus of claim 28, wherein said deployment control comprises a graspable object for moving said aspiration pathway between said deployed position and said retracted position.

30. The disposable integrated thrombectomy and aspiration apparatus of claim 28, further comprising the housing containing a portion of said maceration wire and said aspiration pathway, said motor, one or more of a deployment track, and a power source whereby said housing allows a user to operate and manipulate said apparatus, said deployment track defining a pathway along which said deployment control will move between said deployed position and said retracted position.

31. The disposable integrated thrombectomy and aspiration apparatus of claim 30, wherein said deployment track includes a plurality of mechanical restraints being configured to removably secure said deployment control in either said deployed position or said retracted position.

32. The disposable integrated thrombectomy and aspiration apparatus of claim 23, further comprising the housing containing a portion of said maceration wire and said aspiration pathway, said motor, and a power source whereby said housing allows a user to operate and manipulate said apparatus.

33. The disposable integrated thrombectomy and aspiration apparatus of claim 32, further comprising a maceration control positioned on said housing being configured to actuate said motor to rotate said maceration wire, said maceration control being positioned on said housing at a trigger finger position so as to allow a user to actuate said maceration control without repositioning a user's hand during operation or positioning.

34. The disposable integrated thrombectomy and aspiration apparatus of claim 33, wherein said housing has a hand-grip size and shape whereby the user can actuate said maceration control and manipulate said housing with one hand.

35. The disposable integrated thrombectomy and aspiration apparatus of claim 23, further comprising a maceration control configured to actuate said motor to rotate said maceration wire.

36. The disposable integrated thrombectomy and aspiration apparatus of claim 23, further comprising a catheter being removably coupled to said catheter connection port via a catheter coupler and covering a portion of said maceration wire, said catheter further including a flexible sheath extending distally in said axial direction away from said catheter coupler, said flexible sheath having an inside surface and a distal opening positioned opposite of said catheter coupler, said inside surface and said maceration wire defining a catheter annular portion of said aspiration pathway whereby said inside surface is of sufficient size to allow the macerated particulate to be aspirated from said distal opening toward said aspiration pump connection port of said apparatus, said catheter being slideably engaged with said maceration wire.

37. The disposable integrated thrombectomy and aspiration apparatus of claim 36, further comprising an auxiliary injection port being fluidly coupled to said catheter, whereby said auxiliary injection port allows injectable solutions to enter said catheter annular portion of said aspiration pathway.

38. The disposable integrated thrombectomy and aspiration apparatus of claim 23, wherein the catheter connection port is removably coupled to a disposable integrated thrombectomy and aspiration catheter, said catheter comprising:

a catheter coupler whereby said catheter is removably coupled to an apparatus providing either or both of aspiration or maceration;

a flexible sheath extending distally in an axial direction away from said catheter coupler, said flexible sheath having an inside surface and a distal opening positioned opposite of said catheter coupler; and an aspiration pathway extending between said catheter coupler and said distal opening whereby macerated particulate may pass through a catheter annular portion defined as a boundary between said inside surface of said flexible sheath and said maceration wire whereby the macerated particulate may be aspirated from the patient, said catheter annular portion allowing said flexible sheath to be slidably engaged with said maceration wire.

39. The disposable integrated thrombectomy and aspiration catheter of claim 38, wherein said inside surface of said flexible sheath has a diameter between 5 F and 20 F, whereby said catheter annular portion allows said maceration wire to pass through said flexible sheath and to rotate within said flexible sheath while not obstructing said aspiration pathway.

40. The disposable integrated thrombectomy and aspiration apparatus of claim 38, further comprising an auxiliary injection port being fluidly coupled to said catheter, whereby said auxiliary injection port allows outside materials to enter said catheter annular portion of said aspiration pathway.

41. A disposable thrombectomy maceration and aspiration system for macerating and aspirating thrombus or other obstructive material in a lumen of a vascular graft or vessel, said system comprising:

a disposable integrated aspiration pump and fluid collection device comprising:

a base having a base compartment;

a pump located in said base compartment, said pump includes an intake port and an exhaust port;

a fluid collection compartment located above said base;

a column extends within said fluid collection compartment in substantially a vertical direction, said column includes a lower portion and an upper portion, said column having a cavity connected to said base compartment;

a manifold is located at said upper portion of said column, said manifold includes one or more inlets said manifold includes a generally disc shaped portion, said generally disc shape portion including a lower surface which includes said one or more inlets, whereby said one or more inlets face in a downward direction;

a suction tube includes a first end and a second end, said first end of said suction tube is in fluid communication with said intake port of said pump, said suction tube extends through said cavity of said column, and said second end of said suction tube is in fluid communication with said one or more inlets;

a disposable integrated thrombectomy and aspiration apparatus being removably coupled to said disposable integrated aspiration pump and fluid collection device, said apparatus comprising:

a maceration wire extending in an axial direction;

a motor operatively connected to said maceration wire;

an aspiration pathway extending between a catheter connection port and an aspiration pump connection port and including an interior surface, at least a portion of said aspiration pathway including an annular portion defined as a boundary between said interior surface of said aspiration pathway and said maceration wire whereby macerated particulate may be aspirated from a patient, at least a portion of said interior surface being slidable in relation to said maceration wire, said maceration wire extending through said catheter connection port, said aspiration pathway receiving vacuum pressure from said aspiration pump and fluid collection device;

a housing having the aspiration pump connection port at a proximal end of the housing and the catheter connection port at a distal end of the housing, wherein the aspiration pathway extends in an axial direction between the catheter connection port and the aspiration pump connection port; and a catheter being removably coupled to said catheter connection port via a catheter coupler and covering a portion of said maceration wire, said catheter further including a flexible sheath extending in said axial direction away from said catheter coupler, said flexible sheath having an inside surface and a distal opening positioned opposite of said catheter coupler, said inside surface and said maceration wire defining a catheter annular portion of said aspiration pathway whereby said inside surface is of sufficient size to allow the macerated particulate to be aspirated from said distal opening through said disposable integrated thrombectomy and aspiration apparatus and into said fluid collection compartment of said disposable integrated aspiration pump and fluid collection device, said catheter being slideably engaged with said maceration wire.

* * * * *